United States Patent
Himes et al.

(10) Patent No.: US 10,617,657 B2
(45) Date of Patent: Apr. 14, 2020

(54) DEVICES AND METHODS FOR SUSTAINED TREATMENT OF BLADDER PAIN AND IRRITATIVE VOIDING

(71) Applicant: Allergan, Inc., Irvine, CA (US)

(72) Inventors: Julie Himes, Lexington, MA (US); Dennis Giesing, Lee's Summit, MO (US); Cheryl Larrivee-Elkins, Framingham, MA (US); Michael J. Cima, Winchester, MA (US); Purnanand Sarma, Concord, MA (US); Paul Goldenheim, Cambridge, MA (US)

(73) Assignee: Allergan, Inc., Irvine, CA (US)

( * ) Notice: Subject to any disclaimer, the term of this patent is extended or adjusted under 35 U.S.C. 154(b) by 119 days.

(21) Appl. No.: 14/801,059

(22) Filed: Jul. 16, 2015

(65) Prior Publication Data
US 2015/0374645 A1 Dec. 31, 2015

Related U.S. Application Data

(62) Division of application No. 13/347,513, filed on Jan. 10, 2012, now Pat. No. 9,114,111.

(60) Provisional application No. 61/431,334, filed on Jan. 10, 2011, provisional application No. 61/551,923, filed on Oct. 26, 2011.

(51) Int. Cl.
| | |
|---|---|
| *A61K 31/167* | (2006.01) |
| *A61M 25/00* | (2006.01) |
| *A61M 31/00* | (2006.01) |
| *A61K 9/00* | (2006.01) |

(52) U.S. Cl.
CPC .......... *A61K 31/167* (2013.01); *A61M 25/00* (2013.01); *A61M 31/002* (2013.01); *A61K 9/0034* (2013.01)

(58) Field of Classification Search
CPC ... A61K 9/0034; A61K 9/0036; A61M 25/00; A61M 31/002
See application file for complete search history.

(56) References Cited

U.S. PATENT DOCUMENTS

| | | |
|---|---|---|
| 3,854,480 A | 12/1974 | Zaffaroni |
| 3,888,975 A | 6/1975 | Ramwell |

(Continued)

FOREIGN PATENT DOCUMENTS

| | | |
|---|---|---|
| DE | 3332156 A1 | 3/1985 |
| EP | 0572932 A2 | 12/1993 |

(Continued)

OTHER PUBLICATIONS

Nickel, J.C., et al., "Intravesical alkalinized lidocaine (PSD597) offers sustained relief from symptoms of interstitial cystitis and painful bladder syndrom" BJUI International, 103(7):910-18 (Apr. 2009).

(Continued)

*Primary Examiner* — Quynh-Nhu H. Vu
(74) *Attorney, Agent, or Firm* — Lorenz Siddiqi

(57) ABSTRACT

Devices and methods are provided for treating a patient having bladder pain and/or irritative voiding symptoms. The method includes administering to the patient's bladder lidocaine or another anesthetic agent continuously over a treatment period of 24 hours or more in an amount effective to achieve a therapeutic effect which is sustained beyond the end of the treatment period.

16 Claims, 16 Drawing Sheets

(56) References Cited

U.S. PATENT DOCUMENTS

| | | |
|---|---|---|
| 3,901,232 A | 8/1975 | Michaels et al. |
| 3,935,860 A | 2/1976 | Hoff |
| 4,016,251 A | 4/1977 | Higuchi et al. |
| 4,235,236 A | 11/1980 | Theeuwes |
| 4,392,848 A | 7/1983 | Lucas et al. |
| 4,449,980 A | 5/1984 | Millar et al. |
| 4,475,916 A | 10/1984 | Himmelstein |
| 4,629,449 A | 12/1986 | Wong |
| 4,655,219 A | 4/1987 | Petruzzi |
| 4,678,463 A | 7/1987 | Millar |
| 4,871,542 A | 10/1989 | Vilhardt |
| 4,968,507 A | 11/1990 | Zentner et al. |
| 5,366,738 A | 11/1994 | Rork et al. |
| 5,441,550 A | 8/1995 | Hassenboehler, Jr. et al. |
| 5,499,997 A | 3/1996 | Sharpe et al. |
| 5,516,522 A | 5/1996 | Peyman et al. |
| 5,551,954 A | 9/1996 | Buscerni et al. |
| 5,709,874 A | 1/1998 | Hanson et al. |
| 5,788,980 A | 8/1998 | Nabahi |
| 5,795,591 A | 8/1998 | Lee et al. |
| 5,797,898 A | 8/1998 | Santini, Jr. et al. |
| 5,830,230 A | 11/1998 | Berryman et al. |
| 5,851,217 A | 12/1998 | Wolff et al. |
| 5,855,906 A | 1/1999 | McClay |
| 5,869,081 A | 2/1999 | Jackanicz et al. |
| 5,972,372 A | 10/1999 | Saleh et al. |
| 5,989,581 A | 11/1999 | Groenewegen |
| 6,039,968 A | 3/2000 | Nabahi |
| 6,083,933 A | 7/2000 | Hahn |
| 6,086,909 A | 7/2000 | Harrison et al. |
| 6,139,535 A | 10/2000 | Greelis et al. |
| 6,171,298 B1 | 1/2001 | Matsuura et al. |
| 6,183,461 B1 | 2/2001 | Matsuura et al. |
| 6,207,180 B1 | 3/2001 | Ottoboni et al. |
| 6,293,923 B1 | 9/2001 | Yachia et al. |
| 6,398,718 B1 | 6/2002 | Yachi et al. |
| 6,416,780 B1 | 7/2002 | Passmore et al. |
| 6,444,224 B1 | 9/2002 | Rathbone et al. |
| 6,464,999 B1 | 10/2002 | Huo et al. |
| 6,482,837 B1 | 11/2002 | Wood |
| 6,491,666 B1 | 12/2002 | Santini, Jr. et al. |
| 6,682,473 B1 | 1/2004 | Matsuura et al. |
| 6,712,784 B2 | 3/2004 | Huang |
| 6,746,421 B2 | 6/2004 | Yachia et al. |
| 6,749,617 B1 | 6/2004 | Palasis et al. |
| 6,753,011 B2 | 6/2004 | Faour |
| 6,808,522 B2 | 10/2004 | Richards et al. |
| 6,899,890 B2 | 5/2005 | Kirschner et al. |
| 6,932,810 B2 | 8/2005 | Ryan |
| 6,951,654 B2 | 10/2005 | Malcolm et al. |
| 6,976,950 B2 | 12/2005 | Connors et al. |
| 6,988,983 B2 | 1/2006 | Connors et al. |
| 7,005,138 B2 | 2/2006 | Mahashabde et al. |
| 7,074,178 B2 | 7/2006 | Connors et al. |
| 7,521,064 B2 | 4/2009 | Saxena et al. |
| 7,647,112 B2 | 1/2010 | Tracey et al. |
| 7,862,552 B2 | 1/2011 | McIntyre et al. |
| 8,679,094 B2 | 3/2014 | Cima et al. |
| 2003/0059456 A1 | 3/2003 | Malcolm et al. |
| 2003/0118649 A1 | 6/2003 | Gao et al. |
| 2003/0118692 A1 | 6/2003 | Wang et al. |
| 2003/0139800 A1 | 7/2003 | Campbell |
| 2004/0022824 A1 | 2/2004 | Li et al. |
| 2004/0220552 A1 | 11/2004 | Heruth et al. |
| 2004/0260272 A1 | 12/2004 | Friedman et al. |
| 2005/0234013 A1 | 10/2005 | Parsons |
| 2005/0234431 A1 | 10/2005 | Williams et al. |
| 2005/0238733 A1 | 10/2005 | Henry |
| 2006/0105010 A1 | 5/2006 | Rahe et al. |
| 2006/0234978 A1 | 10/2006 | Marcum |
| 2007/0172507 A1 | 7/2007 | Zupkas et al. |
| 2007/0172508 A1 | 7/2007 | Zupkas et al. |
| 2007/0202151 A1 | 8/2007 | Lee et al. |
| 2007/0254014 A1 | 11/2007 | Ahmed et al. |
| 2008/0051740 A1 | 2/2008 | Sokal et al. |
| 2009/0149833 A1* | 6/2009 | Cima ............... A61K 9/0024 604/517 |
| 2010/0003297 A1 | 1/2010 | Tobias et al. |
| 2010/0330149 A1 | 12/2010 | Daniel et al. |
| 2010/0331770 A1 | 12/2010 | Lee et al. |
| 2011/0060309 A1* | 3/2011 | Lee ............... A61K 9/0034 604/500 |
| 2011/0112475 A1 | 5/2011 | Benson |
| 2011/0137244 A1 | 6/2011 | Lee et al. |
| 2011/0152839 A1* | 6/2011 | Cima ............... A61K 31/00 604/517 |
| 2012/0089121 A1 | 4/2012 | Lee et al. |
| 2012/0089122 A1 | 4/2012 | Lee et al. |

FOREIGN PATENT DOCUMENTS

| | | |
|---|---|---|
| JP | 2007196037 | 8/2007 |
| RU | 2390341 | 5/2010 |
| WO | 9843555 | 10/1998 |
| WO | 991884 A1 | 4/1999 |
| WO | 03009882 A2 | 2/2003 |
| WO | 05115245 A1 | 12/2005 |
| WO | 07115259 A2 | 10/2007 |
| WO | 2010151896 | 12/2010 |
| WO | 2012018923 A1 | 2/2012 |
| WO | 2012019155 A1 | 2/2012 |

OTHER PUBLICATIONS

Au et al., Methods to Improve Efficacy of Intravesical Mitomycin C: Results of a Randomized Phase III Trial, Journal of National Cancer Institute, Apr. 18, 2001, 597-604, vol. 93-8, Oxford University Press.

Birch et al., Absorption Characteristics of Lignocaine Following Intravesical Instillation, Scand J. of Urology Nephrol, 1994, 359-364, vol. 28, Scandinavian University Press.

Carr et al., Evaluation of a Transoral Delivery System for Topical Anesthesia, The Journal of the American Dental Association, Dec. 2001, 1714-1719, vol. 132, American Dental Association.

Erickson et al., Interstitial Cystitis, Int. Urogynecol J, 1998, 174-183, vol. 9, Springer-Verlag London Ltd.

Fraser, et al., The Future of Bladder Control—Intravesical Drug Delivery, a Pinch of Pepper, and Gene Therapy, Reviews in Urology, 2002, 1-11, vol. 4, No. 1.

Gammaitoni et al., Safety and Tolerability of the Lidocaine Patch 5%, a Targeted Peripheral Analgesic: A Review of the Literature, The Journal of Clinical Pharmacology, 2003, 111-117, vol. 43, American College of Clinical Pharmacology.

Henry et al., Alkalinized Intravesical Lidocaine to Treat Interstitial Cystitis: Absorption Kinetics in Normal and Interstitial Cystitis Bladders, Urology, Jun. 2001, 119, vol. 57 (Supplemental 6A).

Henry et al., Topical Anesthesia of the Bladder, Abstracts, A61.

Henry et al., Absorption of Alkalized Intravesical Lidocaine in Normal and Inflamed Bladders: A Simple Method for Improving Bladder Anesthesia, The Journal of Urology, Jun. 2001, 1900-1903, vol. 165, American Urological Association, Inc., U.S.A.

Highley et al., Intravesical Drug Delivery Pharmacokinetic and Clinical Considerations, Clinical Pharmacokinet, Jul. 1999, 59-73, vol. 37 (1), Adis International Limited.

Malmstrom, Intravesical Therapy of Superficial Bladder Cancer, Critical Reviews in Oncology Hematology, 2003, 109-126, vol. 47, Elsevier Science Ireland Ltd.

Collins et al., How Common is Prostatitis? A National Survey of Physician Visits. Journal of Urology, 159(4); 1224-1228 (1998).

Curhan et al., Epidemiology of Interstitial Cystitis: A Population Based Study, Journal of Urology, 161(2); 549-552 (1999).

Santus et al, Osmotic Drug Delivery: A Review of the Patent Literature, Journal of Controlled Release 35; 1-21 (1995).

Wright et al. DUROS Osmotic Pharmaceutical Systems for Parenteral & Site-Directed Therapy. Drug Delivery Technology 3(1) 2003.

Wright & Stevenson, Pumps/Osmotic, Encyclopedia of Controlled Drug Delivery, vol. 2, New York; John Wiley (1999) pp. 896-920.

(56) References Cited

OTHER PUBLICATIONS

Parsons et al. Bladder Surface Glycossaminoglycans: An Epithelial Permability Barrier, Journal of Urology, 143 (1); 139-142 (1990).
Parsons, C.L., Successful Downregulation of Bladder Sensory Nerves with Combination of Heparin and Alkalinized Lidocaine in Patients with Interstitial Cystitis, Urology, 65: 45-48 (2005).
Beiko, Urinary Tract Biomaterials, Journal of Urology, vol. 171, 2438-2444, (2004).
Amark, et al., Follow-Up of Long-Time Treatment with Intravesical Oxybutynin for Neurogenic Bladder in Children, Eur Urol. 1998, 148-153, S. Karger AG, Basel.
Burmeister et al., Intravesical Instillation of Trospium Chloride, Oxybutynin and Verapamil for Relaxation of the Bladder Detrusor Muscle. A Placebo Controlled, Randomized Clinical Test, 1998, Abstract.
Walter, et al., Bioavailability of Trospium Chloride After Intravesical Instillation in Patients with Neurogenic Lower Urinary Tract Dysfunction: A Pilot Study, Neurourology and Urodynamics, 1999, 18:447-453, Wiley-Liss, Inc.
Kim et al., Antimuscarinic Agents Exhibit Local Inhibitory Effects on Muscarinic Receptors in Bladder-Afferent Pathways, 2005, 238-242, Elsevier Inc.
Spratt et al., Clinical Delivery System for Intraperitoneal Hyperthermic Chemotherapy, Cancer Research, Feb. 1980 40:256-260.
Theoharides et al, Painful Bladder Syndrome/Interstitial Cystitis: Current Concepts and Role of Nutraceuticals, Seminars in Preventive and Alternative Medicine, 2006, 6-14, vol. 2; Elsevier Inc.
Tyagi, et al., Local Drug Delivery to Bladder Using Technology Innovations, Urological Clinics of North America, 2006, 519-530, vol. 33, Elsevier Inc.
Walker et al., Intravesical Chemotherapy: In Vitro Studies on the Relationship Between Dose and Cytotoxicity, Urological Research, 1986, 137-140, vol. 14, Springer-Verlag.
Verma, et al., Formulation Aspects in the Development of Osmotically Controlled Oral Drug Delivery Systems, Journal of Controlled Released, 2002, 7-27, vol. 79, Elsevier Science B.V.
Li et al., Water Based Silicone Elastomer Controlled Release Tablet Film Coating III—Drug Release Mechanisms, Drug Development and Industrial Pharmacy, 1989, 1943-1968, vol. 15(12), Marcel Dekker, Inc.
Thombre et al., Mechanism of Water Transport in Controlled Porosity Osmotic Devices, Journal of Membrane Science, 1989, 279-310, vol. 40, Elsevier Science Publishers B.V.
Stymne et al., Plasma Concentrations of Lignocaine and Prilocaine after a 24-h Application of Analgesic Cream (EMLA®) to Leg Ulcers, British Journal of Dermatology, 2001, 530-534, vol. 145, British Association of Dermatologists.
Jiranantarat et al., Analgesic Effect of Intraperitoneal Instillation of Bupivacaine for Postoperative Laparoscopic Cholecystectomy, J. Med Assoc Thai, Sep. 2002, 85 (Suppl 3): S897-S903.
Larsson, et al., Effect of Intraperitoneal Instillation of 32% Dextran 70 on Postoperative Adhesion Formation After Tubal Surgery, 1985, Acta Obstet Gynecol Scand 64:437-441.
Potts, Jeanette M., Genitourinary Pain and Inflammation: Diagnosis and Management, 2008, 246-248, Humana Press.
Peters, K. M., Novel Therapy with Intravesical Liposomes for Ulcerative Interstitial Cystitis/Painful Bladder Syndrome, LUTS (2012) 4, 51-53, Blackwell Publishing Asia Pty Ltd.
Peters, K. M., Characterization of a Clinical Cohort of 87 Women with Interstitial Cystitis/Painful Bladder Syndrome, 2008 Elsevier, Inc.—Female Urology—Urology 71 (4) 2008, pp. 634-640.
Pezzone, M.A., Chronic Pelvic Pain and the Overlap of Chronic Pelvic Pain Disorders, International Foundaton for Functional Gastrointestinal Disorders 2007.
Ustinova, E. E., Cross-Talk and Sensitization of Bladder Afferent Nerves, Neurourology and Urodynamics 29:77-81 (2010).
Nikcel, J.C., et al., Continuous Intravesical Lidocaine Treatment for Interstitial Cystitis/Bladder pain Syndrome: Safety and Efficacy of a New Drug Delivery Device, Sci. Transl. Med., 2012, pp. 1-13, 4 (143)
PCT International Search Report & Written Opinion dated Mar. 6, 2012, for PCT/US2012/0280813, filed Jan. 10, 2012, in the name of Taris Biomedical, Inc.
Shulman, L.P., Chronic Pelvic Pain and the Role of Pain of Bladder Origin: Changing the Paradigm to Improve Clinical Outcomes, Int. J. Fertil., 2005, 73-78, 50 (2).
Welk et al., Dyspareunia Response in Patients with Interstitial Cystitis Treated with Intravesical Lidocaine etc., Female Urology, Jan. 30, 2008, 67-70, 71, No. 1, Urology, Belle Mead,, NJ.
Lee, H., et al., An intravesical device for the sustained delivery of lidocaine to the bladder, J. Controlled Release, 2011, 133-139, 149.
Taris Biomedical, View of NCT01150565 on Jun. 24, 2010, Clinical Trails.gov, 2010, retrieved from https://clinicaltrials.goviarchive/NCTO1150565/2010_06_24 on Mar. 28, 2017, pp. 1-3.

\* cited by examiner

DETAIL A

DETAIL A

DEVICES AND METHODS FOR SUSTAINED TREATMENT OF BLADDER PAIN AND IRRITATIVE VOIDING

CROSS-REFERENCE TO RELATED APPLICATIONS

This patent application is a divisional of U.S. application Ser. No. 13/347,513, filed Jan. 10, 2012, which claims the benefit of U.S. Provisional Patent Application No. 61/431,334, filed Jan. 10, 2011, and U.S. Provisional Patent Application No. 61/551,923, filed Oct. 26, 2011. All of these applications are incorporated herein by reference in their entirety.

BACKGROUND

This disclosure is generally in the field of methods and systems for treating bladder pain and irritative voiding symptoms, particularly but not limited to systems and methods using the local, intravesical administration of drug, such as lidocaine, into the bladder, and more particularly to methods and systems for a sustained treatment effect.

Interstitial cystitis (IC) is a urological condition characterized by pain, increased urinary frequency, and urgency. This condition may also involve varying degrees of urinary incontinence and sexual dysfunction. IC and Painful Bladder Syndrome (PBS) include patients with urinary pain not attributable to other causes, such as infection or urinary stones, and are estimated to affect approximately 3 to 8 million people in the U.S. alone, the majority of whom are women (Berry 2009). IC is a serious condition with unmet medical needs.

There is also a need to treat to treat bladder pain and irritative voiding symptoms in non-IC patients. Examples of such non-IC patients include patients with ureteral stents or with painful bladder conditions.

Current treatments for bladder pain include oral medications, such as antimuscarinics, alpha blockers, tricyclics antidepressants, SSRIs, Elmiron, and gabapentin. These drugs may not be effective for some patients. In addition, these oral drugs are delivered systemically, which may cause unwanted side effects and may not achieve therapeutically effective levels in the bladder when at acceptable plasma levels.

Another current treatment includes instillation of a drug (e.g., lidocaine) solution directly into the bladder. Other instillations, such as dimethyl sulfoxide (DMSO), antimuscarinics, heparin, are also known. Another available procedure is hydrodistention. None of these treatments have been shown to be widely effective or to provide a sustained therapeutic benefit.

A number of studies of instillation procedures with lidocaine have been performed in recent years. Nickel et al., BJU International, 103:910-918 (2008) discloses a study in which patients with IC and PBS were studied in a randomized, placebo controlled, double blind fashion, evaluating the effect of 5 daily instillations of an alkalinized solution of lidocaine (200 mg) on efficacy measures of bladder pain and irritative voiding symptoms on Day 8 (three days after completion of treatment) and Day 15 (ten days after completion of treatment.) One efficacy measure that showed improvement at Day 8 (the Interstitial Cystitis Symptom Index or ICSI) did not show sustained improvement at Day 15. Other efficacy measures (bladder pain, urgency, voiding frequency) never showed improvement following treatment when measured either at Day 8 and Day 15 (bladder pain) or only at Day 15 (urgency, voiding frequency). One efficacy measure called the Interstitial Cystitis Problem Index (ICPI) showed improvement both at Day 8 and Day 15, but the effect at Day 15 had diminished somewhat. These findings suggest that instillations of lidocaine into the bladder, even when administered on an aggressive schedule of daily instillation, were not able to show a sustained treatment effect out to 10 days following treatment.

Parsons, Urology 65(1):45-48 (2005) discloses a study in which patients with IC were treated with instillations of alkalinized lidocaine and heparin into the bladder as a single one hour treatment, then followed for 48 hours to assess duration of effect. The paper describes that 94% of patients had relief at 20 minutes following instillation, 50% at 4 hours and 3 of 28 patients (FIG. 1) or ~10% at 48 hours, suggesting a waning of effect over time. Additionally, a set of patients who received three instillations a week for two weeks were assessed at 48 hours following last treatment for durability of effect; 80% reported relief of symptoms; no further follow-up is provided. These findings suggest that the durability of treatment effect for a single lidocaine instillation is approximately 10% at 48 hours.

Henry, et al., J Urology 165:1900-03 (2001) discloses a study in which lidocaine instillations were used in both healthy volunteers (for pharmacokinetic purposes) and IC patients. Pain assessments following a single lidocaine instillation showed duration of effect to be approximately 24 hours: the mean pain score prior to treatment was 6.0. Immediately following treatment this decreased to 1.8. The next day, mean pain had increased up to 3.7. This was again reduced to 1.2 with a second instillation. These results support those seen in the Parsons and Nickel publications, suggesting that the duration of treatment effect with intravesical solutions of lidocaine are 24 to 48 hours.

It would be desirable to provide improved methods for treating patients suffering from bladder pain and irritative voiding symptoms. In particular, it would be desirable to provide a means for providing a sustained treatment effect for several days or weeks or more beyond the active treatment period.

SUMMARY

Improved methods of treating a patient having bladder pain and/or irritative voiding symptoms are provided. In one embodiment, the method includes administering to the patient's bladder lidocaine or another anesthetic agent continuously over a treatment period of 24 hours or more in an amount effective to achieve a therapeutic effect which is sustained beyond the end of the treatment period, as it has been discovered that a sustained treatment effect of bladder pain and irritative voiding symptom beyond the end of the active treatment period can be achieved by providing continuous intravesical treatment with lidocaine. Essentially any means of delivering the lidocaine into the bladder can be used so long as provides therapeutically effective amounts of lidocaine to the bladder continuously over the treatment period of 24 hours or more. The continuous lidocaine treatment over multiple days is also effective to improve bladder mucosal abnormalities (pathological and inflammatory features). This method of treatment not only provides the patient with pain relief and a reduction in urgency during the treatment period, but also surprisingly provides an extended benefit well beyond the end of treatment. In another aspect, a method of treating a patient having bladder pain and/or irritative voiding symptoms is provided that includes administering lidocaine to the patient in an amount effective to achieve a measurable plasma concentration of lidocaine in the patient continuously over a treatment period of at least 24 hours.

DETAILED DESCRIPTION

Figure 1:
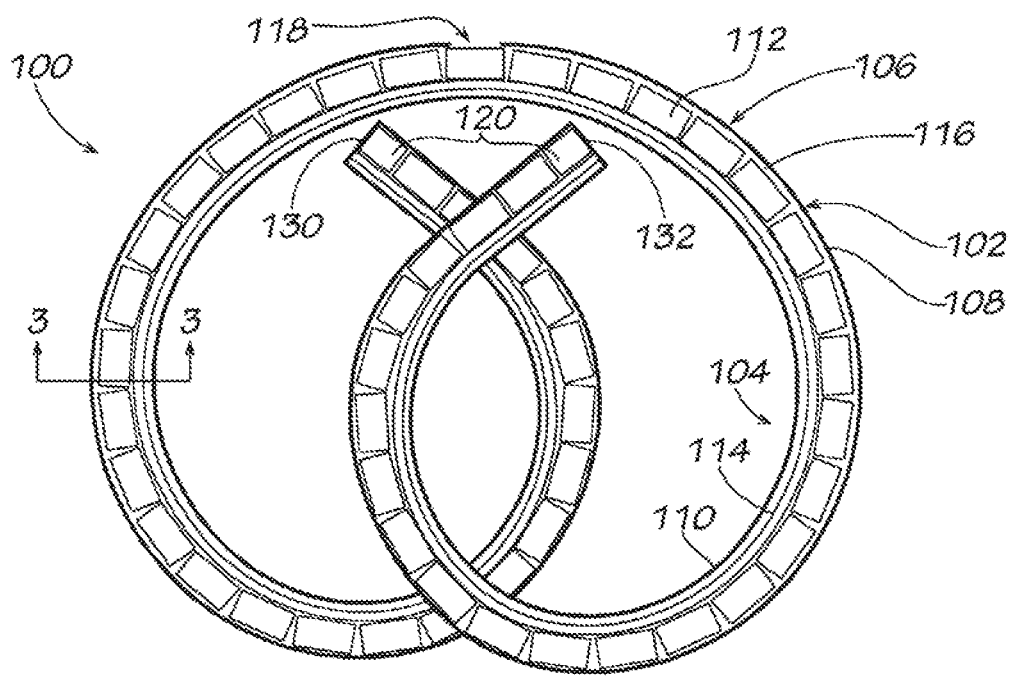
FIG. 1 is a plan view of an embodiment of a drug delivery device.

It has been discovered that a sustained treatment effect of bladder pain and irritative voiding symptom can be achieved by providing continuous intravesical treatment with lidocaine (or other cocaine analogue or another anesthetic agent) over a period of 24 hours or more. Essentially any means of delivering the lidocaine into the bladder can be used so long as provides therapeutically effective amounts of lidocaine to the bladder continuously over the treatment period of 24 hours or more. The continuous lidocaine treatment over multiple days is also effective to improve bladder mucosal abnormalities (pathological and inflammatory features). This method of treatment not only provides the patient with pain relief and a reduction in urgency during the treatment period, but also surprisingly provides an extended benefit well beyond the end of treatment.

As used herein, the term "continuous" or "continuously" in reference to the act of administering to the patient therapeutically effective amounts of the drug for treatment means includes constant or continual release or intermittent release so long as a non-zero plasma level of the lidocaine or other anesthetic agent is maintained over the treatment period, e.g., at least 24 hours. As used herein, the phrases "non-zero plasma level" and "measurable plasma concentration" refer to the low limit of detection using the bioanalytical HPLC method as known in the art.

As used herein, the phrases "amount effective to achieve a therapeutic effect which is sustained beyond the end of the treatment period", "sustained treatment effect", or "sustained therapeutic effect" refer to and include at least a 20% improvement or baseline reduction in at least one of the following 7 or more days after the treatment period ends: baseline bladder pain, baseline bladder urgency, or the number of patients scoring their symptoms as "moderately improved" or "markedly improved" in a Global Response Assessment (GRA) test. In certain embodiments, at least a 35% reduction of baseline bladder pain 7 or more days after the treatment period ends may be achieved. In one embodiment, at least a 40% reduction of baseline bladder pain 7 or more days after the treatment period ends may be achieved. In another embodiment, at least a 45% reduction of baseline bladder pain 7 or more days after the treatment period ends may be achieved. In a further embodiment, at least a 50% reduction of baseline bladder pain 7 or more days after the treatment period ends may be achieved.

In certain embodiments, at least a 45% reduction of baseline bladder urgency 7 or more days after the treatment period ends may be achieved. In one embodiment, at least a 50% reduction of baseline bladder urgency 7 or more days after the treatment period ends may be achieved. In another embodiment, at least a 55% reduction of baseline bladder urgency 7 or more days after the treatment period ends may be achieved. In a further embodiment, at least a 60% reduction of baseline bladder urgency 7 or more days after the treatment period ends may be achieved.

In certain embodiments, at least 35% of patients score their symptoms in a GRA test as "moderately improved" or "markedly improved" 7 or more days after the treatment period ends. In one embodiment, at least 40% of patients score their symptoms in a GRA test as "moderately improved" or "markedly improved" 7 or more days after the treatment period ends. In another embodiment, at least 45% of patients score their symptoms in a GRA test as "moderately improved" or "markedly improved" 7 or more days after the treatment period ends. In a further embodiment, at least 50% of patients score their symptoms in a GRA test as "moderately improved" or "markedly improved" 7 or more days after the treatment period ends.

In one embodiment, the continuous treatment may be provided by deploying a drug delivery device into the bladder of the patient that can release lidocaine into the bladder continuously over a period greater than one day, for example from 2 to 28 days, from 3 to 21 days, or from 10 to 14 days. In one embodiment, the method includes releasing a mean average of from about 10 mg to about 15 mg lidocaine (FBE) per day (e.g., about 11 mg, about 12 mg per day) over a 14-day treatment period.

In one particular variation of this embodiment, the cumulative amount of lidocaine (FBE) released continuously over a 14-day period is approximately 130 mg. In one embodiment, the rate of lidocaine (FBE) released into bladder from the device over this period is from 15 mg to 30 mg day per day over the first 1 to 4 days and then tapering off, for example at a rate of from 15 mg to 3 mg per day over the remainder of the active treatment period. At the end of the treatment period, the device can be retrieved from the bladder.

In one embodiment where lidocaine is administered, the measurable plasma concentration of lidocaine does not exceed 65 ng/ml at a time of peak lidocaine exposure in the bladder, for example with the 650 mg lidocaine device described in Example 2 below. With smaller payload devices or systems releasing lidocaine at a lower rate, the measurable plasma concentration of lidocaine at a time of peak lidocaine exposure may be even lower, for example not exceeding 50 ng/ml, 40 ng/ml, 25 ng/ml, or 15 ng/ml.

In another embodiment, the continuous treatment may include pumping a lidocaine solution into the bladder through a urethral catheter in a continuous or pulsatile manner over the treatment period. It is noted that a single instillation (bolus) of lidocaine per day would not be expected to provide continuous treatment over a 24-hour period, as the patient would be likely to urinate away any unabsorbed lidocaine before the end of the period. In still another embodiment, a coating substance may be locally applied to the bladder wall, wherein the coating substance includes lidocaine and one or more excipient materials that promote adherance of the coating substance to the wall of the bladder and provides continuous controlled release of the lidocaine over the treatment period.

In some embodiments, the coating substance is a mucoadhesive formulation. Examples of mucoadhesive formulations include, but are not limited to, gels, ointments, creams, films, emulsion gels, tablets, polymers, or a combination thereof. Mucoadhesive formulation polymers may include hydrogels or hydrophilic polymers, polycarbophil (i.e. Carbopols, etc.), chitosan, polyvinylpyrrolidone (PVP), lectin, polyethyleneglycolated polymers, celluloses, or a combination thereof. Suitable celluloses include methyl cellulose (MC), carboxymethyl cellulose (CMC), hydroxypropyl cellulose (HPC), or combinations thereof.

In some embodiments, the coating substance is or can include a permeation enhancer. Non-limiting examples of permeation enhancers include dimethyl sulfoxide (DMSO), sodium carboxymethyl cellulose (NaCMC), lipids, surfactants, or combinations thereof.

In other embodiments, the method may include releasing or pumping a greater or lesser cumulative amount of lidocaine over the treatment period.

It is also envisioned that a topical sustained release system, such as a transdermal patch, may be used to continuously deliver the lidocaine or other anesthetic agent regionally or systemically to a patient in need of treatment of IC and/or irritative voiding for 24 hours or more to achieve a sustained treatment effect.

The devices and methods disclosed herein build upon those described in U.S. Application Publication No. 2010/0331770, (TB 101); U.S. Application Publication No. 2010/03300149 (TB 102); U.S. Application Publication No. 2011/0060309 (TB 108); and U.S. Application Publication No. 2011/0152839 (TB 112), which are incorporated herein by reference.

The term "patient" refers to humans, whether male or female, adult or child, and may further include other mammals, such as in veterinary or livestock applications.

The Implantable Drug Delivery Device

An embodiment of a drug delivery device 100 is illustrated in FIG. 1. The device 100 includes a drug reservoir portion 102 and a retention frame portion 104. In FIG. 1, the device 100 is shown in a relatively expanded shape suited for retention in the body, and in FIG. 2 the device 100 is shown in a relatively lower-profile shape for deployment through the channel 200 of a deployment instrument, such as a cystoscope or other catheter. Following deployment into the body, the device 100 may assume the relatively expanded shape to retain the drug delivery device in the body cavity or lumen.

For the purposes of this disclosure, terms such as "relatively expanded shape," "relatively higher-profile shape," or "retention shape" generally denote any shape suited for retaining the device in the intended implantation location, including but not limited to the pretzel shape shown in FIG. 1 that is suited for retaining the device in the bladder. Similarly, terms such as "relatively lower-profile shape" or "deployment shape" generally denote any shape suited for deploying the drug delivery device into the body, including the linear or elongated shape shown in FIG. 2 that is suited for deploying the device through the working channel of catheter, cystoscope, or other deployment instrument positioned in a lumen of the body, such as the urethra. In embodiments, the drug delivery device may naturally assume the relatively expanded shape and may be deformed, either manually or with the aid of an external apparatus, into the relatively lower-profile shape for insertion into the body. Once deployed the device may spontaneously or naturally return to the initial, relatively expanded shape for retention in the body.

In the illustrated embodiment, the drug reservoir and retention frame portions 102, 104 of the drug delivery device 100 are longitudinally aligned and are coupled to each other along their length, although other configurations are possible. For example, the drug reservoir portion 102 may be attached to the retention frame portion 104 at discrete points but otherwise may be separate or spaced apart from the retention frame portion 104.

In particular, the drug delivery device 100 includes an elastic or flexible device body 106 that defines a drug reservoir lumen 108 and a retention frame lumen 110. The drug reservoir lumen 108 is designed to house a drug formulation, such as a number of solid drug tablets 112, to form the drug reservoir portion 102. The retention frame lumen 110 is designed to house a retention frame 114 to form the retention frame portion 104. The illustrated lumens 108, 110 are discrete from each other, although other configurations are possible.

Figure 3:
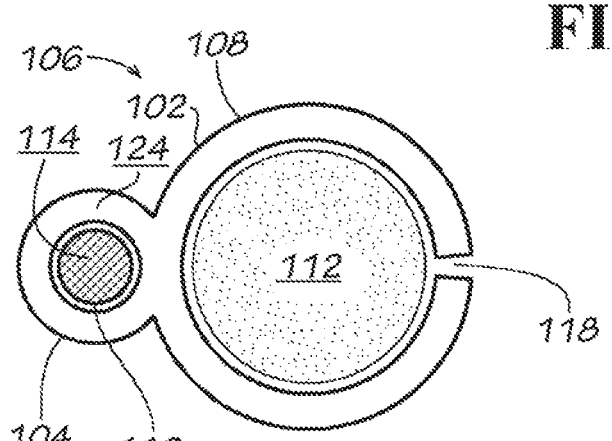
FIG. 3 is a cross-sectional view of the drug delivery device shown in FIG. 1, taken along line 3-3 in FIG. 1.

As shown in the cross-sectional view of FIG. 3, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The device body 106 may be formed integrally, such as via molding or extrusion, although separate construction and assembly of the tubes 122, 124 is possible. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. Further, the two walls 122, 124 are attached along the entire length of the device in the illustrated embodiment, although intermittent attachment can be employed.

An aperture 118 may be formed through the wall 124 that defines the drug reservoir lumen 108. The aperture 118 may provide a passageway for releasing drug from the drug reservoir lumen 108 as further described below. However, the aperture 118 may be omitted in some embodiments.

As shown in FIG. 1, the drug reservoir lumen 108 is loaded with a number of drug units 112 in a serial arrangement. For example, between about 10 and about 100 drug units 112 may be loaded, such as between about 30 and about 70 drug units 112, or more particularly between about 50 and 60 drug units 112. However, any number of drug units may be used. The drug reservoir lumen 108 includes an entry 130 and an exit 132, which are shown as relatively circular openings at opposite ends of the drug reservoir lumen 108. The entry 130 provides ingress for the drug units 112 to be placed into the drug reservoir lumen 108 during device loading and assembly, such as by a flow of pressurized gas, in which case the exit 132 provides egress for the flow of pressurized gas to escape from the drug reservoir lumen 108. Once the drug units 112 are loaded, at least two end plugs 120 block the entry 130 and exit 132. The end plugs 120 may be cylindrical plugs inserted into the entry 130 and the exit 132, each having a slightly larger outer diameter than an inner diameter of the drug reservoir lumen 108 so that the plugs substantially enclose the entry 130 and exit 132 and are snugly retained in position. In some cases, a number of end plugs 120 can be positioned in the entry 130 or the exit 132. The end plugs 120 may be silicone plugs. The end plugs 120 also may be omitted, in which case the entry 130 and exit 132 may be closed with a material, such as adhesive, that is placed in the drug reservoir lumen 108 in workable form and cures therein.

In some embodiments, the drug tablets 112 may not fill the entire drug reservoir lumen 108. In such embodiments, a filling material may be used to fill the remainder of the drug reservoir lumen 108. For example, the drug tablets 112 may be loaded in a central portion of the drug reservoir lumen 108 and the filling material may be loaded in the remaining end portions of the drug reservoir lumen 108. The filling material may be inserted into the end portions of the drug reservoir lumen 108 after the lumen is filled with the drug tablets 112. The filling material may be a polymeric material. The polymeric material may be placed in the drug reservoir lumen 108 in workable form and may cure therein. Suitable polymeric materials may cure at room temperature or in response to an external stimulus, such as heat. In some cases, the filling material may enclose the entry 130 and exit 132, in which case the end plugs 120 may or may not be provided. The filling material also may be a number of end plugs 120 inserted into the end portions of the drug reservoir lumen 108.

Once the drug units 112 are loaded, interstices 116 or breaks may be formed between adjacent drug units 112. The interstices or breaks 116 may serve as reliefs that accommodate deformation or movement of the device 100, while permitting the individual drug units 112 to retain their solid form during storage and deployment. Thus, the drug delivery device 100 may be relatively flexible or deformable despite being loaded with a solid drug, as each drug unit 112 may be permitted to move with reference to adjacent drug units 112. Along the length of the device drug reservoir lumen 108, the drug units 112 may have the same composition or may vary in composition, and in some cases drug units 112 of different compositions may be in distinct reservoirs that are segregated, either axially or radially, along the length of the drug reservoir lumen 108.

The retention frame lumen 110 is loaded with the retention frame 114, which may be an elastic wire. The retention frame 110 may be configured to spontaneously return to a retention shape, such as the illustrated "pretzel" shape or another coiled shape. In particular, the retention frame 114 may retain the device 100 in the body, such as in the bladder. For example, the retention frame 114 may have an elastic limit and modulus that allows the device 100 to be introduced into the body in a relatively lower-profile shape, permits the device 100 to return the relatively expanded shape once inside the body, and impedes the device from assuming the relatively lower-profile shape within the body in response to expected forces, such as the hydrodynamic forces associated with contraction of the detrusor muscle and urination. Thus, the device 100 may be retained in the body once implanted, limiting or prevent accidental expulsion.

The material used to form the device body 106 may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases. The flexible material also allows the device body 106 to flex outward or circumferentially expand in response to a flow of pressurized gas through the drug reservoir lumen 108 during drug loading, as described below. The material used to form the device body 106 also may be water permeable or porous so that solubilizing fluid can enter the drug reservoir portion 102 to solubilize the drug units 112 once the device is implanted. For example, silicone or another biocompatible elastomeric material may be used.

In one embodiment in which the drug delivery device 100 is designed to be implanted in the bladder, the drug delivery device 100 is designed to be inserted into (and optionally retrieved from) the bladder through the urethra cystoscopicly. Thus, the device may be sized and shaped to fit through a narrow tubular path of a deployment instrument, such as a catheter or cystoscope.

In one embodiment in which the drug delivery device is designed to be implanted in the bladder, the drug delivery device is designed to be inserted into the bladder through the urethra via cystoscope. Thus, the device may be sized and shaped to fit through a narrow tubular path of a deployment instrument, such as a catheter or cystoscope.

Typically, a cystoscope for an adult human has an outer diameter of about 5 to 7 mm and a working channel having an inner diameter of about 2.4 mm to about 2.6 mm. In other embodiments, a cystoscope has a working channel with a larger inner diameter, such as an inner diameter of 4 mm or more. Thus, the device may be relatively small in size. For example, when the device is elastically deformed to the relatively lower profile shape, the device for an adult patient may have a total outer diameter that is about 3.75 mm or less, such as about 2.6 mm or less. For pediatric patients, the dimensions of the device are anticipated to be smaller. In addition to permitting insertion, the relatively small size of the device may also reduce patient discomfort and trauma to the bladder.

The overall configuration of the device preferably is designed to ensure that the device is tolerable to the patient while it is deployed in vivo, as described in U.S. Patent Application Publication No. 2011/0152839 A1 to Cima et al., which is incorporated herein by reference. The device geometry may be customized to avoid or minimized undesirable contact forces and pressures linked to urgency sensation. Within the three-dimensional space occupied by the device in the retention shape, the maximum dimension of the device in any direction is less than 10 cm, the approximate diameter of the bladder when filled. In some embodiments, the maximum dimension of the device in any direction may be less than about 9 cm, such as about 8 cm, 7 cm, 6 cm, 5 cm, 4.5 cm, 4 cm, 3.5 cm, 3 cm, 2.5 or smaller. In particular embodiments, the maximum dimension of the device in any direction is less than about 7 cm, such as about 6 cm, 5 cm, 4.5 cm, 4 cm, 3.5 cm, 3 cm, 2.5 cm or smaller. In preferred embodiments, the maximum dimension of the device in any direction is less than about 6 cm or smaller.

More particularly, the three-dimension space occupied by the device is defined by three perpendicular directions. Along one of these directions the device has its maximum dimension, and along the two other directions the device may have smaller dimensions. For example, the smaller dimensions in the two other directions may be less than about 4 cm, such as about 3.5 cm, 3 cm, or less. In a preferred embodiment, the device has a dimension in at least one of these directions that is less than 3 cm.

The overall shape of the device may enable the device to reorient itself within the bladder to reduce its engagement or contact with the bladder wall. For example, the overall exterior shape of the device may be curved, and all or a majority of the exterior or exposed surfaces of the device may be substantially rounded. The device also may be substantially devoid of sharp edges, and its exterior surfaces may be formed from a material that experiences reduced frictional engagement with the bladder wall. Such a configuration may enable the device to reposition itself within the empty bladder so that the device applies lower contact pressures to the bladder wall. In other words, the device may slip or roll against the bladder wall into a position in which the device experiences less compression. In embodiments, the device may not be fixed to one location within the bladder, i.e., it may move freely within the bladder, which without being bound to any particular theory is believed at least in part to contribute to the device's quality of being tolerable or even unnoticeable in human bladders.

Figure 9:
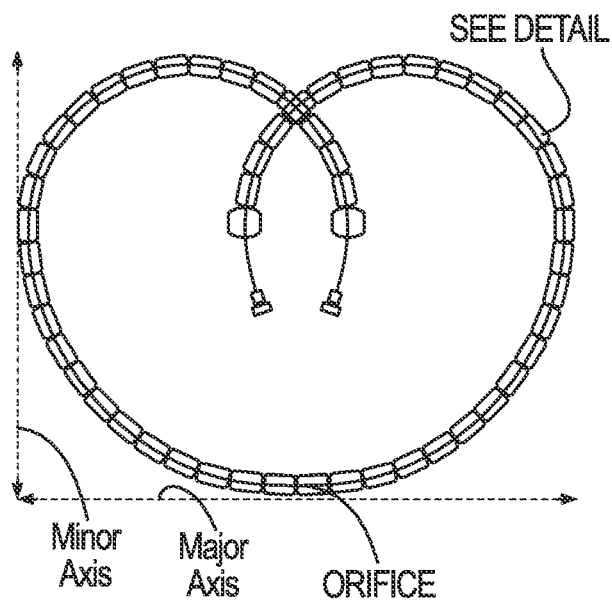
FIG. 9 is a detailed cross-sectional plan view of an embodiment of a drug delivery device.
Figure 9A:
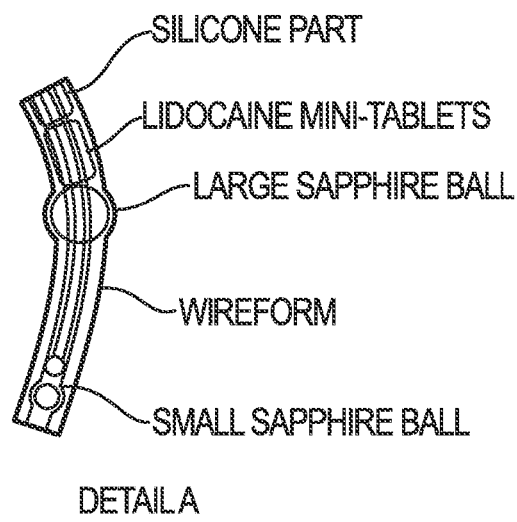
Figure 10:
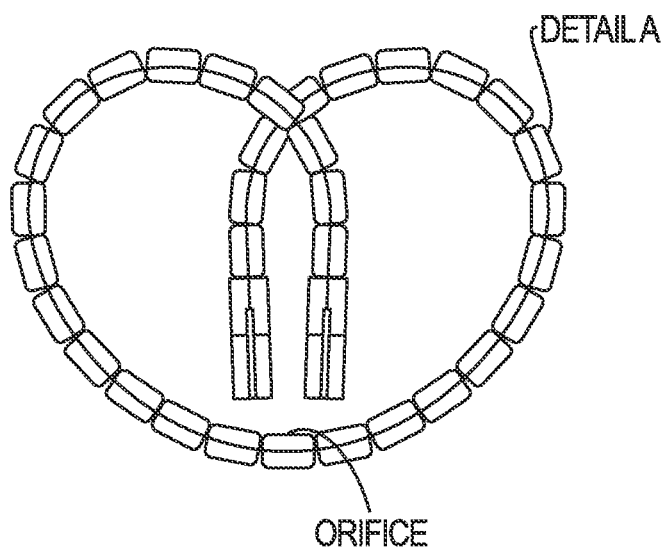
FIG. 10 is a detailed cross-sectional plan view of another embodiment of a drug delivery device.
Figure 10A:
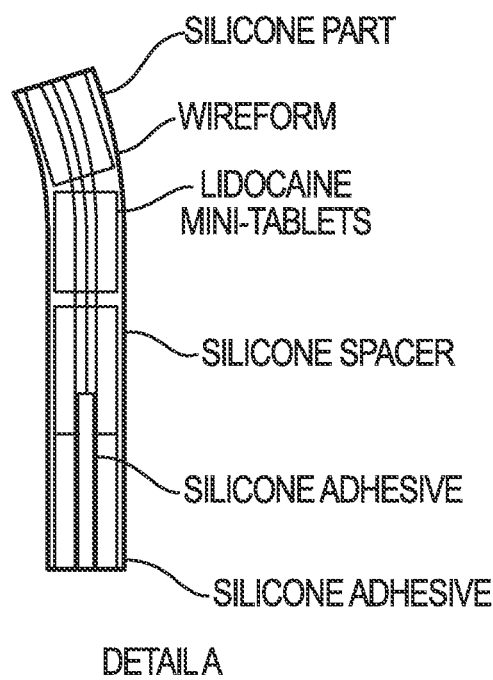

An example of a device that generally satisfies these characteristics is shown in FIGS. 1, 9, and 10. In particular, the illustrated devices are generally planar in shape even though the device occupies three-dimensional space. Such devices may define a minor axis, about which the device is substantially symmetrical, and a major axis that is substantially perpendicular to the minor axis. The device may have a maximum dimension in the direction of the major axis that does not exceed about 6 cm, and in particular embodiments is less than 5 cm, such as about 4.5 cm, about 4 cm, about 3.5 cm, about 3 cm, or smaller. The device may have a maximum dimension in the direction of the minor axis that does not exceed about 4.5 cm, and in particular embodiments is less than 4 cm, such as about 3.5 cm, about 3 cm, or smaller. The device is curved about substantially its entire exterior perimeter in both a major cross-sectional plane and a minor cross-sectional plane. In other words, the overall exterior shape of the device is curved and the cross-sectional shape of the device is rounded. Thus, the device is substantially devoid of edges, except for edges on the two flat ends, which are completely protected within the interior of the device when the device lies in a plane. These characteristics enable the device to reorient itself into a position of reduced compression when in the empty bladder.

The device also may be small enough in the retention shape to permit intravesical mobility. In particular, the device when deployed may be small enough to move within the bladder, such as to move freely or unimpeded throughout the entire bladder under most conditions of bladder fullness, facilitating patient tolerance of the device. Free movement of the device also facilitates uniform drug delivery throughout the entire bladder, as opposed to a particular bladder location located near the release orifice. However, devices that otherwise move freely within the bladder may be impeded from moving freely when the bladder is empty, and yet the device may still be tolerable if sufficiently compressible as described above.

The device also may have a density that is selected to facilitate floatation. The device has a minimum density in a dry and unloaded state, meaning the device is not loaded with drug and fluid is not present in the device walls or lumens. The density of the device also increases when the device is in a wet state, meaning fluid is present in the device walls and lumens. The device enters the wet state upon implantation in the bladder, as the device becomes surrounded by urine. In use, the device may have a maximum density after implantation, when the device is loaded with the maximum drug payload and liquid displaces any air present in the walls and lumens. Subsequently, the density of the device may remain essentially the same or decrease as the drug is solubilized and released, and replaced by urine.

In general, the device in the dry and loaded state may have a density in the range of about 0.5 g/mL to about 1.5 g/mL, such as between about 0.7 g/mL to about 1.3 g/mL. In some embodiments, the device in the dry and loaded has a density that is less than the density of water, such as a density that is less than about 1 g/mL. Such densities facilitate buoyancy and movement in the bladder. Lighter or lower density materials may be integrated into the device as needed to compensate for any higher density drug or other payload in the device, thereby maintaining an overall density that facilitates buoyancy for tolerance purposes. In addition, air or another gas may be trapped in portions of the device to reduce the overall density. For example, the walls of retention frame lumen may be made impermeable to water such that an air pocket is formed in the retention frame lumen about the elastic wire. A coating or sheath may be applied to the walls, on either the inside or outside, to reduce the water permeability.

One example device may have a mass of about 0.40 grams or less and a density of about 0.7 g/mL or less when unloaded. The device may be loaded with a drug having a mass of about 275 mg or less. In such embodiments, the device when loaded may have a mass of about 0.675 grams or less and a density of about 1.1 g/mL or less. Such a device may be well tolerated in the bladder. Devices of smaller masses and densities would likewise be well tolerated. The device may also be somewhat larger, for example, the L650 device described in Example 3 below.

The exact configuration and shape of the intravesical drug delivery device may be selected depending upon a variety of factors including the specific site of deployment/implantation, route of insertion, drug, dosage regimen, and therapeutic application of the device. The design of the device may minimize the patient's pain and discomfort, while locally delivering a therapeutically effective dose of the drug to a tissue site (e.g., urothelial tissue) in a patient.

The implantable drug delivery device can be made to be completely or partially bioerodible so that no explantation, or retrieval, of the device is required following release of the drug formulation. As used herein, the term "bioerodible" means that the device, or part thereof, degrades in vivo by dissolution, enzymatic hydrolysis, erosion, resorption, or a combination thereof. In one embodiment, this degradation occurs at a time that does not interfere with the intended kinetics of release of the drug from the device. For example, substantial erosion of the device may not occur until after the drug formulation is substantially or completely released. In another embodiment, the device is erodible and the release of the drug formulation is controlled at least in part by the degradation or erosion characteristics of the erodible device body.

Alternatively, the implantable drug delivery device may be at least partially non-bioerodible. In some embodiments, the device is formed from materials suited for urological applications, such as medical grade silicone, natural latex, PTFE, ePTFE, PLGA, PGS, stainless steel, nitinol, elgiloy (non ferro magnetic metal alloy), polypropylene, polyethylene, polycarbonate, polyester, nylon, or combinations thereof. Following release of the drug formulation, the device and/or the retention frame may be removed substantially intact or in multiple pieces. In some embodiments, the device is partially bioerodible so that the device, upon partial erosion, breaks into non-erodible pieces small enough to be excreted from the bladder. In another embodiment, the device may be collapsible following drug release, thereby facilitating voiding of the device in a substantially intact form. Useful biocompatible erodible and non-erodible materials of construction are known in the art.

In a preferred embodiment, the drug delivery device is sterilized, such as after the device is manufactured/assembled and before the device is implanted. In some cases, the device may be sterilized after the device is packaged, such as by subjecting the package to gamma irradiation or ethylene oxide gas.

The Drug Reservoir Portion

In one embodiment, the drug reservoir portion of the device includes an elongated tube. An interior of the tube may define one or more drug reservoirs, and a drug formulation may be housed in the drug reservoir(s). In another embodiment, the drug reservoir portion is in a form other than a tube.

The release rate of the drug from the drug reservoir portion generally is controlled by the design of the combination of the device components, including but not limited to the materials, dimensions, surface area, and apertures of the drug reservoir portion, as well as the particular drug formulation and total mass of drug load, among others.

Figure 2:
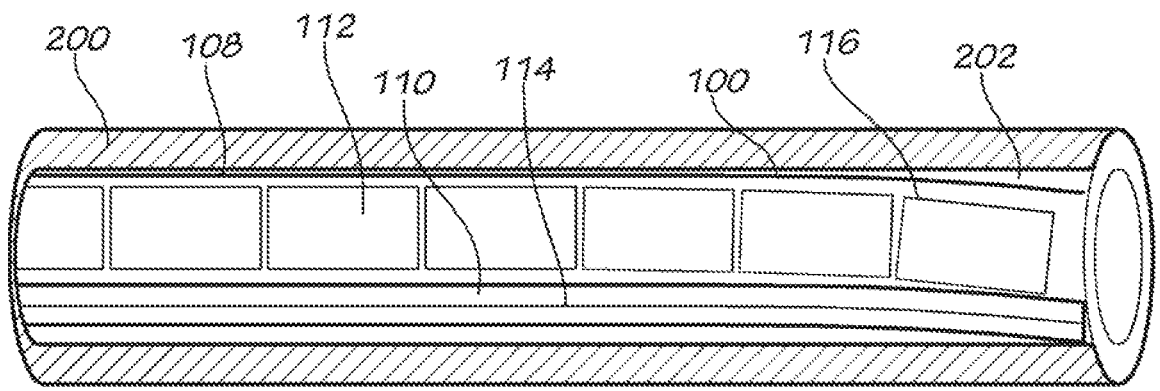
FIG. 2 is a plan view of the drug delivery device shown in FIG. 1, illustrating the drug delivery device inside a deployment instrument.

An example of such a drug reservoir portion is shown in FIGS. 1-3. As shown, the drug reservoir portion 102 may include a body formed from an elastomeric tube 122. The tube 122 defines a reservoir 108 that contains a number of drug tablets 112. Ends of the tube 122 may be sealed with sealing structures 120. At least one aperture 118 may be disposed in the tube 122. In cases in which an aperture 118 is provided, the aperture 118 may be closed by a degradable timing membrane, which may control the initiation of release of the drug formulation from the reservoir. In some cases, a sheath or coating may be positioned about at least a portion of the tube 122 to control or reduce the release rate, such as by reducing the osmotic surface area of the tube or by reducing diffusion through the tube wall. For simplicity, the degradable timing membranes and sheaths or coatings are not shown.

In one embodiment, the drug reservoir portion operates as an osmotic pump. In such embodiments, the tube may be formed from a water permeable material, such as a silicone, or tube may have a porous structure, or both. Following implantation, water or urine permeates through the wall of the tube, one or more apertures formed through the tube, or one or more passing pores formed through a porous tube. The water enters the reservoir, and is imbibed by the drug formulation. Solubilized drug is dispensed at a controlled rate out of the reservoir through the one or more apertures, driven by osmotic pressure in the reservoir. The delivery rate and overall performance of the osmotic pump is affected by device parameters, such as the surface area of the tube; the permeability to liquid of the material used to form the tube; the shape, size, number and placement of the apertures; and the drug formulation dissolution profile, among other factors. The delivery rate can be predicted from the physicochemical parameters defining the particular drug delivery system, according to well known principles, which are described, for example, in Theeuwes, *J. Pharm. Sci.*, 64(12): 1987-91 (1975). In some embodiments, the device may initially exhibit a zero-order release rate and subsequently may exhibit a reduced, non-zero-order release rate, in which case the overall drug release profile may be determined by the initial zero-order release rate and the total payload. Representative examples of osmotic pump designs, and equations for selecting such designs, are described in U.S. Patent Publication No. 2009/0149833.

In an alternative embodiment, the device may operate essentially by diffusion of the drug from the tube through (i) one or more discrete apertures formed in the wall of the tube, or passing pores formed in the wall of a porous tube, or (ii) through the wall of the tube itself, which may be permeable to the drug, or (iii) a combination thereof. In embodiments in which diffusion occurs through the wall, the apertures or passing pores may not be included. In still other embodiments, the device may operate by a combination of osmosis and diffusion.

The drug reservoir portion may be formed from an elastomeric material, which may permit elastically deforming the device for its insertion into a patient, e.g., during its deployment through deployment instrument such as a cystoscope or catheter. For example, the tube may be elastically deformed along with the retention frame for intravesical implantation, as described in further detail below.

In preferred embodiments, the drug reservoir portion is formed from a material that is both elastomeric and water permeable. One material that is both elastomeric and water permeable is silicone, although other biocompatible materials may be used.

The length, diameter, and thickness of the tube may be selected based on the volume of drug formulation to be contained, the desired rate of delivery of the drug from the tube, the intended site of implantation of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device.

In one embodiment, the device body is non-resorbable. It may be formed of a medical grade silicone tubing, as known in the art. Other examples of suitable non-resorbable materials include synthetic polymers selected from poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene) and other fluorinated polymers, poly(siloxanes), copolymers thereof, and combinations thereof.

In some embodiments, the device body is bioerodible. In one embodiment of a bioerodible device, the tube of the body is formed of a biodegradable or bioresorbable polymer. Examples of suitable such materials include synthetic polymers selected from poly(amides), poly(esters), poly(ester amides), poly(anhydrides), poly(orthoesters), polyphosphazenes, pseudo poly(amino acids), poly(glycerol-sebacate) (PGS), copolymers thereof, and mixtures thereof. In a preferred embodiment, the resorbable synthetic polymers are selected from poly(lactic acids), poly(glycolic acids), poly(lactic-co-glycolic acids), poly(caprolactones), and mixtures thereof. Other curable bioresorbable elastomers include poly(caprolactone) (PC) derivatives, amino alcohol-based poly(ester amides) (PEA) and poly(octane-diol citrate) (POC). PC-based polymers may require additional cross-linking agents such as lysine diisocyanate or 2,2-bis($\epsilon$-caprolacton-4-yl)propane to obtain elastomeric properties.

The tube of a drug reservoir portion tube may be substantially linear and in some cases may be substantially cylindrical with a circular cross-section, although square, triangle, hexagon, and other polygonal cross-sectional shapes can be used, among others.

The ends of the tube may be sealed to limit escape of the drug, such as with a sealing structure or other sealing means. The sealing structure may have any shape suited to plug or close the tube end, such as a cylinder 120 as shown in FIG. 1, a ball, a disk, or others. In some embodiments, the sealing structure may have a larger diameter than the inner diameter of the tube, such that the tube stretches to fit snugly about the sealing structure, closing the tube and retaining the sealing structure in place. The sealing structure may be formed from biocompatible material, including a metal such as stainless steel, a polymer such as silicone, a ceramic, sapphire, or adhesive, among others or combinations thereof. The material may be biodegradable or bioerodible. A medical grade silicone adhesive or other adhesive also may be loaded into the tube in a workable form and may then cure within the tube to seal the end.

In some embodiments, the tube may have multiple reservoirs. Each reservoir may be defined by a portion of the tube inner surface and at least one partition. The partition may be a partition structure or plug inserted into the tube, such as a cylinder, sphere, or disk, among others, in which case the partition structure may have a larger cross-section than the tube, securing the partition structure in place and segregating adjacent reservoirs. For example, the cylindrical plug 120 of FIG. 1 that closes the tube end may instead serve as a partition structure to segregate two reservoirs positioned adjacent to each other along the length of the tube. The partition may be non-porous or semi-porous, non-resorbable or resorbable and may be formed of a material described above with reference to the cylindrical plug 120. The partition also may be formed in the tube, such as by molding. For example, one or more webs may extend through the tube along its length to segregate axial reservoirs that extend along the length of the tube, as shown in Examples J through L of FIG. 6. The partition also may be a structure that joins two different tubes that serve as separate reservoirs, as shown in Examples M through O of FIG. 6.

The multiple reservoirs permit segregating two or more different drug formulations in different reservoirs, delivering a single drug from different reservoirs at different rates or times following implantation, or combinations thereof. For example, two different reservoirs may have different configurations, such as different materials, different permeabilities, different numbers or placements of apertures (or the absence of apertures), different timing membranes in the apertures, among others or combinations thereof. The two different reservoirs also may house the same or different drug formulations in the same or different forms (such as liquid, semi-solid, and solid), or combinations thereof. The two different reservoirs further may be configured to release drug via different release mechanisms, such as via osmosis through an aperture and by diffusion through a drug reservoir wall that may lack an aperture completely. Coatings or sheaths also may be provided along different portions of a single drug reservoir or along different drug reservoirs housing the same or different drug formulations. These embodiments can be combined and varied to achieve the desired release profile of the desired drug.

For example, the onset of release of two doses in different reservoirs can be staged by configuring the device accordingly, such as by using different materials for portions of the tube defining different reservoirs, by associating the aperture(s) of different reservoirs with different timing membranes, by placing drugs with different solubilities in the reservoirs, or by placing drugs with different forms in the reservoirs, such as a liquid form for immediate release and a solid form to be solubilized prior to release. Thus, the device may release some drug relatively quickly after implantation while other drug may experience an induction time before beginning release.

In one embodiment, the total volume of the reservoir (or combined reservoirs) is sufficient to contain all the drug needed for local delivery over the course of a single treatment, reducing the number of procedures needed to treat a particular condition.

Apertures

In some embodiments, the device includes one or more apertures or orifices for dispensing the drug, such as via osmosis, diffusion, or a combination thereof, among other. The apertures may be spaced along the tube to provide a passageway for release of the drug formulation. The apertures or orifices may be positioned through a sidewall or an end of the tube. The apertures may be in fluid communication with one or more reservoirs. Embodiments of apertures 118 are shown on the drug reservoir portions in FIGS. 1 and 3.

The aperture may be located about a middle of the drug reservoir portion or adjacent to its exit, which may affect the ease of loading solid drug units into the drug reservoir portion as described below. The apertures may be positioned away from a portion of the tube that will be folded during insertion to limit tearing of degradable membranes on the apertures.

In embodiments in which the device includes a device body that defines both drug reservoir and retention frame lumens, such as the embodiment shown in FIG. 3, the aperture or apertures may have various positions on the wall of the drug reservoir lumen with reference to the wall of the retention frame lumen, as further described below.

The size, number, and placement of the apertures may be selected to provide a controlled rate of release of the drug. A device that operates primarily as an osmotic pump may have one or more apertures sized small enough to reduce diffusion of the drug through the aperture(s), yet large enough and spaced appropriately along the tube to reduce the buildup of hydrostatic pressure in the tube. Within these constraints, the size and number of apertures for a single device (or reservoir) can be varied to achieve a selected release rate. In exemplary embodiments, the diameter of the aperture is between about 20 μm and about 500 μm, such as between about 25 μm and about 300 μm, and more particularly between about 30 μm and about 200 μm. In one particular example, the aperture has a diameter between about 100 μm and about 200 μm, such as about 150 μm. In embodiments where the device operates primarily by diffusion, the apertures may be in this range or larger. A single device may have apertures of two or more different sizes. The aperture may be circular, although other shapes are possible and envisioned, with the shape typically depending on manufacturing considerations. Examples of processes for forming the apertures include mechanical punching, laser drilling, laser ablation, and molding. The aperture may slightly taper from an exterior to an interior of the tube, and the aperture may be created either before or after the drug is loaded into the tube. The aperture also may be formed in an orifice structure disposed in an end of the tube, such as a ruby or sapphire precision orifice structure from, for example, Bird Precision Orifices, Swiss Jewel Company.

In some embodiments, the drug reservoir portion may not have any apertures, in which case the drug may be released via a release mechanism other than osmosis, such as diffusion through the wall of the drug reservoir portion. Similarly, a drug reservoir portion having multiple discrete drug reservoirs may have apertures associated with all, some, or none of the drug reservoirs, in which cases release from the different drug reservoirs may occur via different release mechanisms.

In one embodiment, a degradable membrane, i.e., a timing membrane, is disposed over or in the apertures (e.g., in register with the aperture) to control the onset of release of the drug formulation. The degradable membrane may be a coating over all or some of the outer surface of the tube or a discrete membrane above or within the aperture. Two or more degradable membranes also may be used to control release from one aperture. The membranes may be formed, for example, of a resorbable synthetic polymer (such as polyester, a poly(anhydride), or a polycaprolactone) or a resorbable biological material (such as cholesterol, other lipids and fats). Additional details are described in U.S. Publication No. 2009/0149833.

The Drug Formulation and Solid Drug Units

The drug formulation can include essentially any therapeutic, prophylactic, or diagnostic agent, such as one that would be useful to deliver locally to a body cavity or lumen or regionally about the body cavity or lumen. The drug formulation may consist only of the drug, or one or more pharmaceutically acceptable excipients may be included. The drug may be a biologic. The drug may be a metabolite. As used herein, the term "drug" with reference to any specific drug described herein includes its alternative forms, such as salt forms, free acid forms, free base forms, and hydrates. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug.

In a preferred embodiment, the drug formulation is in a solid or semi-solid form in order to reduce the overall volume of the drug formulation and thereby reduce the size of the device, facilitating implantation. The semi-solid form may be, for example, an emulsion or suspension; a gel or a paste. In many embodiments, the drug formulation desirably includes no or a minimum quantity of excipient for the same reasons of volume/size minimization.

In some embodiments, the drug is a high solubility drug. As used herein, the term "high solubility" refers to a drug that has a solubility above about 10 mg/mL water at 37° C. In other embodiments, the drug is a low solubility drug. As used herein, the term "low solubility" refers to a drug that has a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility. One example is lidocaine, which has a high solubility of about 680 mg/mL when in the form of a lidocaine hydrochloride monohydrate, a water-soluble salt, but has a low solubility of about 8 mg/mL when in the form of lidocaine base. High solubility drugs may be suited for release due to an osmotic pressure gradient, such as via one or more apertures or passing pores through the device wall, while low solubility drugs may be suited for release via diffusion, such as directly through the device wall or through one or more apertures or passing pores in the device wall. Thus, the drug may be formulated to have a high or low solubility depending on the intended release mode. In one embodiment, the drug is formulated to improve its apparent solubility in the implantation environment, such as its apparent solubility in urine within the bladder.

In a particular embodiment, the devices provide pain relief to the patient. A variety of anesthetic agents, analgesic agents, and combinations thereof may be used. In embodiments, the device delivers one or more local anesthetic agents. The local anesthetic agent may be a cocaine analogue. In particular embodiments, the local anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These local anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The anesthetic agent may be provided in combination with other drugs, such as those described in U.S. Patent Application Publication No. 2011/0152839 A1 to Cima, et al., which is incorporated herein by reference.

The analgesic agent may be a narcotic or non-narcotic agent. Representative examples of analgesics include acetaminophen, buprenorphine, butorphanol, codeine, dihydrocodeine, fentanyl, heroin, hydrocodone, hydromorphone, methadone, morphine, nicomorphine, oxycodone, oxymorphone, pentazocine, pethidine, propoxyphene, pyridium (phenazopyridine), thebaine, tramadol, In certain embodiments, the drug delivery device is used to treat inflammatory conditions such as interstitial cystitis, radiation cystitis, painful bladder syndrome, prostatitis, urethritis, post-surgical pain, and kidney stones. In one particular embodiment, the drug delivery device is used in association with the placement of a ureteral stent, such as to treat pain, urinary urgency or urinary frequency resulting from ureteral stent placement.

The excipient of the drug formulation may be a matrix material, selected to modulate or control the rate of release of the drug from the reservoir. In one embodiment, the matrix material may be a resorbable or non-resorbable polymer. In another embodiment, the excipient comprises a hydrophobic or amphiphilic compound, such as a lipid (e.g., a fatty acids and derivatives, mono-, di- and triglycerides, phospholipids, sphingolipids, cholesterol and steroid derivatives, oils, vitamins and terpenes). The drug formulation may provide a temporally modulated release profile or a more continuous or consistent release profile. Other drugs and excipients may be used for other therapies.

In some embodiments, the drug formulation is in solid form. For example, the drug formulation is formed into solid drug units that are loaded into the drug reservoir portion. Each of the drug units is a solid, discrete object that substantially retains a selectively imparted shape (at the temperature and pressure conditions to which the delivery device normally will be exposed during assembly, storage, and handling before implantation). The drug units may be in the form of tablets, capsules, pellets, or beads, although other configurations are possible. For example, FIGS. 1 and 2 illustrate a number of the solid drug units 112 that are suited for implantation loaded into the drug reservoir lumen 108 of the drug delivery device 100.

The solid drug units may be made by a direct compression tableting process, a molding process, or other processes known in the pharmaceutical arts. The solid drug unit may be a tablet or capsule. The tablet optionally may be coated with one or more materials known in the art for protecting the tablets against destructive exposure to oxygen or humidity during tablet handling, device assembly and storage; for facilitating device loading; for aesthetics; or for facilitating, retarding, or otherwise controlling in vivo dissolution and drug release characteristics. The drug formulation also may be loaded into the drug reservoir in workable form and may cure therein. Thereafter, the solidified drug may be broken along the length of the drug reservoir to form the interstices or breaks that permit device deformation. For example, in embodiments in which the drug formulation is configured to be melted and solidified, the drug formulation can be melted, injected into the drug reservoir in melted form, solidified in the drug reservoir, and broken into pieces in the drug reservoir to accommodate device deformation or movement. The drug formulation also may be extruded with the drug reservoir, may cure within the drug reservoir, and subsequently may be broken along the length of the reservoir to accommodate device deformation. In another form, the drug unit may be in a semi-solid form.

The drug tablet includes a drug content and may include an excipient content. The drug content includes one or more drugs or active pharmaceutical ingredients (API), while the excipient content includes one or more excipients. The term "excipient" is known in the art, and representative examples of excipients useful in the present drug units may include ingredients such as binders, lubricants, glidants, disintegrants, colors, fillers or diluents, coatings and preservatives, as well as other ingredients to facilitate manufacturing, storing, or administering the drug units.

In order to maximize the amount of drug that can be stored in and released from a given drug delivery device of a selected (small) size, the drug unit preferably comprises a high weight fraction of drug or API, with a reduced or low weight fraction of excipients as are required for tablet manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a drug tablet that has 90% by weight of a drug in salt form may include less than 90% by weight of that drug in free base form.

In one embodiment, the drug tablet is more than 50% by weight drug. In a preferred embodiment, 75% or more of the weight of the drug tablet is drug, with the remainder of the weight comprising excipients, such as lubricants and binders that facilitate making the drug tablet. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the drug tablet. In some cases, the drug content comprises about 75% or more of the weight of the drug tablet. More particularly, the drug content may comprise about 80% or more of the weight of the drug tablet. For example, the drug content may comprise between about 85% and about 99.9% of the weight of the drug tablet. In some embodiments, the excipient content can be omitted completely.

In one embodiment, the drug and excipients are selected and the tablet formulated to be water soluble, so that the drug tablets can be solubilized when the device is located within the vesical, to release the solubilized drug. In a preferred embodiment, the drug tablets are formulated to be sterilizable, either within or outside of the drug delivery device, without substantial or detrimental changes in the chemical or physical composition of the drug tablets. Such drug tablets may be quite different from conventional drug tablets, which typically include active ingredients that constitute less than 50% of the drug tablet content by weight, with the remainder of the drug tablet comprising excipients that are often insoluble and/or may not be suited for conventional sterilization. Furthermore, the present drug tablets may be sized and shaped for use with an implantable drug delivery device. For example, the drug tablets may be "mini-tablets" that are much smaller in size than conventional tablets, which may permit inserting the drug tablets through a lumen such as the urethra into a cavity such as the bladder. An embodiment of a solid drug tablet 112 for intravesical insertion or other in vivo implantation is shown in FIGS. 1-3. In a preferred embodiment, the drug tablets are mini-tablets which comprise greater than 80% lidocaine hydrochloride monohydrate.

In embodiments in which one or more pharmaceutically acceptable excipients are included, the excipients may facilitate loading the solid drug units in the device. For example, the excipients may increase the lubricity of the drug units so that the drug units can slide with reference to the interior lumen walls of the drug reservoir portion. The excipients also may facilitate forming the therapeutic agent or agents into a solid drug tablet that can be loaded into the drug reservoir portion. The excipients also may affect the kinetics of drug release from the device, such as by increasing or retarding the solubility or dissolution rate of the drug units. In some embodiments, however, the drug release rate is predominately controlled by characteristics of the drug reservoir, such as the tube thickness and permeability to water or urine, while the excipient content of the drug units is primarily selected to permit reliable production of drug units that are solid and include a relatively high weight fraction of drug.

The individual drug units may have essentially any selected shape and dimension that fits within the device. In one embodiment, the drug units are sized and shaped such that the drug reservoir portion is substantially filled by a select number of drug units. Each drug unit may have a cross-sectional shape that substantially corresponds to a cross-sectional shape of the drug reservoir portion. For example, the drug units 112 are substantially cylindrical in shape as shown in FIGS. 1 and 3 for positioning in the substantially cylindrical drug reservoir lumen 108 shown in FIG. 1. Once loaded, the drug units 112 substantially fill the drug reservoir lumen 108, forming the drug reservoir portion 102.

The drug units may have outer dimensions that are about the same as, are slightly less than, or slightly exceed inner dimensions of the drug reservoir portion. The drug unit 112 shown in FIGS. 1-3 has an outer diameter that slightly exceeds an inner diameter of the drug reservoir lumen 108 shown in FIG. 3. Such drug units 112 may be loaded into the lumen 108 under a flow of pressurized gas that radially expands the drug reservoir wall 122 so that the drug units 112 may travel through the drug reservoir lumen 108 in an axial direction, and when the flow of pressurized gas is removed, the wall 122 may return to retain the drug units 112 in selected axial positions along the length of the lumen 108, as shown in FIG. 1.

In embodiments, the drug units are shaped to align in a row when housed in the drug reservoir. Each drug unit has a cross-sectional shape that corresponds to the cross-sectional shape of the drug reservoir, and each drug unit may have end face shapes that correspond to the end faces of adjacent drug units. Thus, once the drug tablets are loaded in the drug reservoir, the line or row of drug tablets may substantially fill the drug reservoir with interstices or breaks formed between adjacent drug units. The interstices or breaks accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

An example is shown in FIGS. 1-3, which illustrates the drug unit 112 having circular flat end faces and a cylindrical side wall. Thus, the drug unit 112 can be aligned in a row with other drug units 112 for loading into the cylindrical drug reservoir lumen 108 as shown in FIGS. 1 and 2. When so loaded, the drug units 112 substantially fill the drug reservoir lumen 108, with interstices or breaks 116 formed between them to accommodate deformation or movement. The flat end faces permit piecewise flexibility of the device while limiting the volume or space within the drug reservoir portion that is devoted to the interstices or breaks 116. Thus, the device can be substantially filled with solid drug while retaining its flexibility. Loading the device with a number of drug tablets 112, such as drug tablets that are relatively uniform in size and shape, beneficially permits manufacturing a device that behaves as expected in response to expected forces during and after implantation and exhibits expected drug release characteristics once implanted. That is, the tablet uniformity advantageously enables reproducibility in producing the medical product and thereby generally provides reliable, repeatable drug release characteristics.

In embodiments in which the solid drug tablets are designed for insertion or implantation in a lumen or cavity in the body, such as the bladder, via a drug delivery device, such as a device of the type described above with reference to FIGS. 1-3, the drug tablets may be "mini-tablets" that are suitably sized and shaped for insertion through a natural lumen of the body, such as the urethra. For the purpose of this disclosure, the term "mini-tablet" generally indicates a solid drug tablet that is substantially cylindrical in shape, having end faces that are relatively planar or flat and a side face that is substantially cylindrical. An example mini-tablet is shown in FIG. 1. The mini-tablet 112 has a diameter, extending along the end face, in the range of about 1.0 to about 3.2 mm, such as between about 1.5 and about 3.1 mm. The mini-tablet has a length, extending along the side face, in the range of about 1.7 mm to about 4.8 mm, such as between about 2.0 mm and about 4.5 mm. The friability of the tablet may be less than about 2%. Embodiments of solid drug tablets and systems and methods of making the same are further described below with reference to U.S. patent applications incorporated by reference herein.

In a preferred embodiment, the drug tablets include lidocaine. A drug delivery device having drug tablets that primarily comprise lidocaine may be wholly deployed in the bladder of a patient in need of treatment for interstitial cystitis, neurogenic bladder, or pain, among others. Other diseases or conditions may also be treated using this device. In other embodiments, other drugs, alone or in combination with lidocaine, may be used to treat interstitial cystitis or other diseases and conditions involving the bladder including pain of the bladder and urethra, spasm of the bladder and urethra, and detrusor instability and voiding frequency and nocturia associated with and following any variety of procedures used to evaluate, diagnosis or treat the bladder, urethra, or prostate gland. In another embodiment, the treatment methods described herein are used to provide post-procedural symptom relief.

Once the solid drug tablets are formed, the drug tablets may be loaded into the drug delivery device. After the device is loaded, the device preferably is sterilized. The selected sterilization process does not undesirably alter the physical or chemical composition of the solid drug tablets or other components of the device. Examples of suitable sterilization processes include gamma irradiation or ethylene oxide sterilization, although other sterilization processes may be used. For example, gamma irradiation at a strength of about 8 KGy to about 40 KGy, such as about 25 KGy, can be employed. Alternatively or in addition, the assembled and loaded device may be made using an aseptic manufacturing process.

In addition, the drug tablets can be sterilized before or after loading/assembly into a drug delivery device, and the drug tablets possess a commercially reasonable shelf life. Once implanted, the composition of the drug tablets is appropriate for the intended route of administration, is stable in acidic conditions, and provides pre-selected, reproducible drug release kinetics. For example, the drug tablets may be solubilized in the bladder to continuously release drug at a suitably stable rate drug over an extended period.

Although mini-tablets and other solid drug tablets are described above as having a high weight fraction of drug or API and a low weight fraction of excipients, the solid drug tablets may have any weight fraction of drug, especially in cases in which the tablet includes a drug that is extremely potent, a stabilizing agent, or an agent that increases the solubility of the drug, among others or combinations thereof.

The Retention Frame Portion

The drug delivery device may include a retention frame portion. The retention frame portion is associated with the drug reservoir portion and permits retaining the drug reservoir portion in the body, such as in the bladder. The retention frame portion may include a retention frame that is deformable between a relatively expanded shape and a relatively lower-profile shape. For example, the retention frame may naturally assume the relatively expanded shape, may be manipulated into the relatively lower-profile shape for insertion into the body, and may spontaneously return to the relatively expanded shape upon insertion into the body. The retention frame in the relatively expanded shape may be shaped for retention in a body cavity, and the retention frame in the relatively lower-profile shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once implanted. Such a configuration may limit or prevent accidental expulsion of the device from the body under expected forces. For example, the device may be retained in the bladder during urination or contraction of the detrusor muscle.

In a preferred embodiment, the retention frame includes or consists of an elastic wire. In one embodiment, the elastic wire may comprise a biocompatible shape-memory material or a biodegradable shape memory polymer as described in U.S. Pat. No. 6,160,084 to Langer et al. The elastic wire also may include a relatively low modulus elastomer, which may be relatively less likely to irritate or cause ulcer within the bladder or other implantation site and may be biodegradable so that the device need not be removed. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

For example, in the embodiment shown in FIGS. 1-2, the retention frame 114 is an elastic wire formed from a superelastic alloy, such as nitinol, and surrounded by the wall 124 of the retention frame lumen 310, which forms a protective sheath about the retention frame 114. Thus, the wall 124 may be formed from a polymer material, such as silicone. In other embodiments, the retention frame may be an elastic wire formed from a superelastic alloy, such as nitinol, that is covered in a polymer coating, such as a silicone sheath and is attached to the drug reservoir portion.

In some embodiments, the retention frame lumen 110 may include the retention frame 114 and a filling material, such as a polymer filling. An example filling material is a silicone adhesive, such as MED3-4213 by Nusil Technology LLC, although other filling materials may be used. The filling material may fill the void in the retention frame lumen 110 about the retention frame 114. For example, the filling material may be poured into the retention frame lumen 110 about the retention frame 114 and may cure therein. The filling material may reduce the tendency of the drug reservoir lumen 108 to stretch along, or twist or rotate about, the retention frame 114, while maintaining the drug reservoir lumen 108 in a selected orientation with reference to the retention frame 114. The filling material is not necessary, however, and may be omitted.

When the retention frame is in the relatively expanded shape, such as the coiled shapes shown in FIG. 1, the device may occupy a space having dimensions suited to impede expulsion from the bladder. When the retention frame is in the relatively lower-profile shape, such as the elongated shapes shown in FIG. 2, the device may occupy an area suited for insertion into the body, such as through the working channel of a deployment instrument. The properties of the elastic wire cause the device to function as a spring, deforming in response to a compressive load but spontaneously returning to its initial shape once the load is removed. The polymer coating may make the outer surface of the retention frame relatively smooth and soft, reducing irritation of the bladder or other implantation site.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame comprises a shape-memory material, the material used to form the frame may "memorize" and spontaneously assume the relatively expanded shape upon the application of heat to the device, such as when exposed to body temperatures upon entering the bladder.

The retention frame may be in a form having a high enough spring constant to retain the device within a body cavity, such as the bladder. A high modulus material may be used, or a low modulus material. Especially when a low-modulus material is used, the retention frame may have a diameter and/or shape that provides a spring constant without which the frame would significantly deform under the forces of urination. For example, the retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m. Such a spring constant may be achieved by one or more of the following techniques: increasing the diameter of the elastic wire used to form the frame, increasing the curvature of one or more windings of the elastic wire, and adding additional windings to the elastic wire. The windings, coils, or spirals of the frame may have a number of configurations. For example, the frame may be in a curl configuration comprising one or more loops, curls or sub-circles. The ends of the elastic wire may be adapted to avoid tissue irritation and scarring, such as by being soft, blunt, inwardly directed, joined together, or a combination thereof.

Examples are shown in FIG. 5. The retention frame may have a two-dimensional structure that is confined to a plane, a three-dimensional structure, such as a structure that occupies the interior of a spheroid, or some combination thereof. In particular, Examples A through G illustrate frames comprising one or more loops, curls, or sub-circles, connected either linearly or radially, turning in the same or in alternating directions, and overlapping or not overlapping. Examples H through N illustrate frames comprising one or more circles or ovals arranged in a two-dimensional or a three-dimensional configuration, the circles or ovals either closed or opened, having the same or different sizes, overlapping or not overlapping, and joined together at one or more connecting points. The retention frame portion also may be a three-dimensional structure that is shaped to occupy or wind about a spheroid-shaped space, such as a spherical space, a space having a prorate spheroid shape, or a space having an oblate spheroid shape. Examples O through R illustrate retention frame portions that are shaped to occupy or wind about a spherical space, with each retention frame portion shown above a representation of the frame in a sphere. The retention frame portion may generally take the shape of two intersecting circles lying in different planes as shown in Example O, two intersecting circles lying in different planes with inwardly curled ends as shown in Example P, three intersecting circles lying in different planes as shown in Example Q, or a spherical spiral as shown in Example R. In each of these examples, the retention frame portion can be stretched to the linear shape for deployment through a deployment instrument. The retention frame portion may wind about or through the spherical space, or other spheroid-shaped space, in a variety of other manners. One or both of the retention frame and retention housing may be omitted, in which case the retention portion may be components of the drug portion itself, which may assume or may be deformed into a retention shape, or the retention portion may be an anchor associated with the drug portion. Examples of alternative configurations are described in the U.S. patent applications incorporated by reference herein.

Other Device Features

The device may include at least one radio-opaque portion or structure to facilitate detection or viewing (e.g., by X-ray imaging or fluoroscopy) of the device by a medical practitioner as part of the implantation or retrieval procedure.

The device may include a retrieval feature, such as a structure that facilitates removal of the device from the body cavity, for example for removal of a non-resorbable device body following release of the drug formulation. One example of a retrieval feature is a string, formed of a biocompatible material. The string may be attached to a mid-portion or an end-portion of the drug delivery device. In some embodiments, the string is sized to extend along the urethra from the bladder to the exterior of the body, in which case a proximal end of the string may be positioned outside of the body once the device is positioned in the bladder. The string also may be shorter in size, so that once the device is positioned in the bladder, the proximal end of the string is positioned in the urethra in a location that is reachable by a physician. In either case, the device may be removed from the bladder by engaging the string to pull the device through the urethra. In other embodiments, the string is sized to be wholly implanted in the bladder with the device, in which case the string facilitates locating and grasping the device within the bladder using a removal instrument positioned in the urethra, such as a cystoscope or catheter.

The drug reservoir portion can include a coating or a sheath, which may be substantially impermeable to water or relatively less permeable to water than the drug reservoir portion to reduce or alter the osmotic or diffusive surface area of the device body, as described in U.S. Patent Publication No. 2009/0149833.

Combination of the Components

The drug reservoir portion and the retention frame portion are associated with each other to form the drug delivery device. A variety of different associations are envisioned. For example, the drug reservoir portion and the retention frame portion may be at least partially aligned. In other words, the drug reservoir portion may extend along a portion or the entire length of the retention frame portion, substantially parallel or coincident with the retention frame portion. An example of such an embodiment is shown in FIGS. 1-3. FIG. 6 also illustrates several alternative embodiments in cross-section. As shown in Examples F, G, H, and I, the retention frame wire may extend along either an exterior surface of the drug reservoir wall, along an interior surface of the drug reservoir wall, through the drug reservoir wall, or within a reinforced area inside or outside of the wall. As shown in Examples J, K, and L, the elastic wire may also be positioned within the interior of the tube supported by a web, which may partition the tube into multiple compartments. The web may be perforated or otherwise non-continuous so that the compartments are in communication with each other, or the web may be relatively continuous such that the compartments are segregated from each other to form different reservoirs that may be suited for holding different drug formulations. The web may be formed from the same material as the tube, or from a material having a different permeability to water or urine, depending on the embodiment. As shown in Examples M, N, and O, the elastic wire may be associated with multiple tubes, extending along or between the tubes. The elastic wire may be embedded in a reinforcement area that joins together multiple discrete tubes. The tubes may hold the same or different drug formulations and also may be formed from the same or different materials of construction, such as materials that differ in permeability to urine or other aqueous or bodily fluids.

In other embodiments, the drug reservoir portion may be attached to only portion of the retention frame. The drug reservoir portion may have first and second end portions that are attached to a portion of the retention frame. The end portions of the drug reservoir may terminate at the retention frame, the end portions may overlap the retention frame, or a combination thereof. The drug reservoir portion may be oriented with reference to the retention frame portion such that the drug reservoir portion lies within the perimeter of the retention frame portion, beyond the perimeter of the retention frame portion, or a combination thereof. Additionally, a number of drug reservoir portions may be associated with a single retention frame portion. Examples A through E of FIG. 6 illustrate such embodiments.

In other embodiments, the drug reservoir portion and the retention frame portion may be the same component in some embodiments. In such cases, the device may comprise a tube formed in a configuration having a sufficient spring constant to retain the device in the body, as described above. Also, the drug reservoir portion may be wrapped around the retention frame portion, one or any number of times. The embodiments described herein may be combined and varied to produce other drug delivery devices that fall within the scope of the present disclosure. For example, the drug reservoir portion may be attached to any portion of the retention frame portion in any manner. Multiple drug reservoir portions may be provided, a single drug reservoir portion may be partitioned, or a combination thereof, which may facilitate delivering multiple different drugs into the body, delivering different forms of drugs into the body, delivering drugs at varying rates into the body, or a combination thereof.

Figure 4:
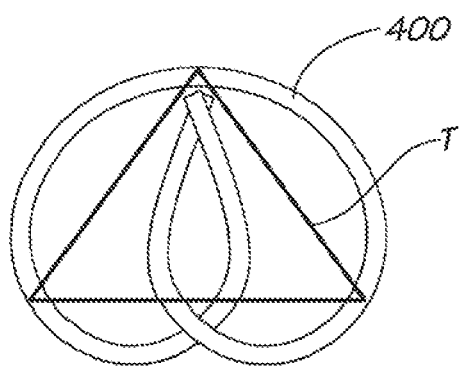
FIG. 4 is an illustration showing the size of an embodiment of a drug delivery device in comparison to an approximation of the bladder trigone region.
Figure 5A:
FIGS. 5A-5R illustrate examples of shapes for a retention frame of a drug delivery device.
Figure 5B:
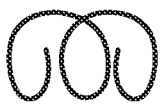
Figure 5C:
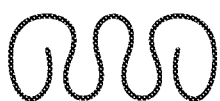
Figure 5D:
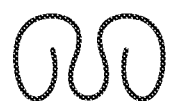
Figure 5E:
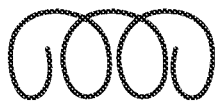
Figure 5F:
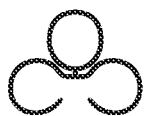
Figure 5G:
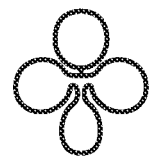
Figure 5H:
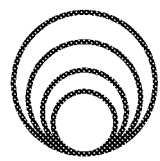
Figure 5I:
Figure 5J:
Figure 5K:
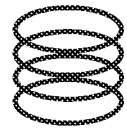
Figure 5L:
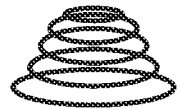
Figure 5M:
Figure 5N:
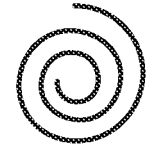
Figure 5O:
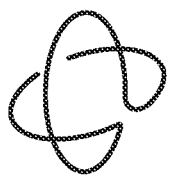
Figure 5P:
Figure 5Q:
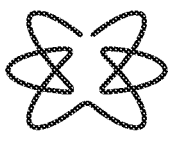
Figure 5R:
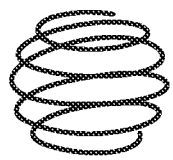
Figure 6A:
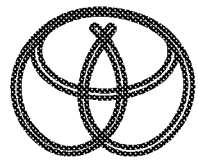
FIGS. 6A-6O illustrate examples of configurations for drug delivery devices having at least one drug delivery portion and a retention frame portion.
Figure 6B:
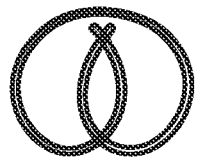
Figure 6C:
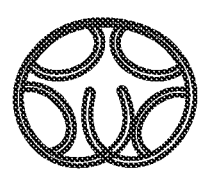
Figure 6D:
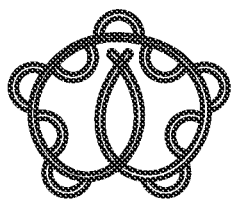
Figure 6E:
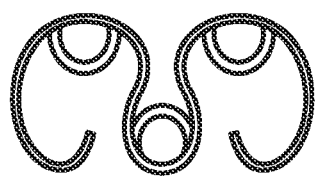
Figure 6F:
Figure 6G:
Figure 6H:
Figure 6I:
Figure 6J:
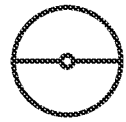
Figure 6K:
Figure 6L:
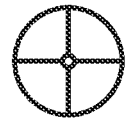
Figure 6M:
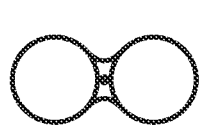
Figure 6N:
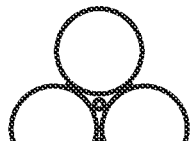
Figure 6O:
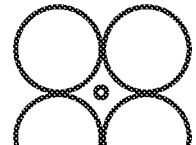

It is noted that the device 400 shown in FIG. 4 has a slightly different shape and configuration than the device 100 shown in FIG. 1. For example, the ends of the device 400 are relatively straighter than the ends of device 100. The straighter ends may result because the retention frame of the device 400 has relatively straight end portions, while the retention frame of the device 100 has relatively curved end portions. A retention frame with relatively straight end portions may be less likely to puncture the walls of the device body during drug loading and thereafter, reducing the risk of device failure after implantation. However, either retention frame shape can be used.

In the embodiment shown in FIG. 1, for example, the drug delivery device 100 is suited for delivering a drug into the bladder. The drug reservoir lumen 108 may have an inner diameter of about 1.3 to about 3.3 mm, such as about 1.5 to about 3.1 mm, an outer diameter of about 1.7 to about 3.7 mm, such as about 1.9 to about 3.4 mm, and a length of about 12 to 21 cm, such as about 14 to 16 cm. The drug reservoir lumen 108 may hold about 10 to 100 cylindrical drug tablets, such mini-tablets. The mini-tablets may each having a diameter of about 1.0 to about 3.3 mm, such as about 1.5 to about 3.1 mm, and a length of about 1.5 to about 4.7 mm, such as about 2.0 to about 4.5 mm. Such mini-tablets may have a lidocaine payload of about 3.0 to about 40.0 mg. One particular example of a mini-tablet may have a diameter of about 1.52 mm, a length of about 2.0 to 2.2 mm, and a mass of about 4.0 to 4.5 mg lidocaine. Another particular example of a mini-tablet may have a diameter of about 2.16 mm, a length of about 2.9 to 3.2 mm, and a mass of about 11.7 to 13.1 mg lidocaine. Yet another particular example of a mini-tablet may have a diameter of about 2.64 mm, a length of about 3.5 to 3.9 mm, and a mass of about 21.3 to 23.7 mg lidocaine. Still another particular example of a mini-tablet may have a diameter of about 3.05 mm, a length of about 4.1 to 4.5 mm, and a mass of about 32.7 to 36.9 mg lidocaine. However, other diameters, lengths, and masses can be used.

Within these ranges, the device may be designed to deliver between about 150 mg and 1000 mg of lidocaine to the bladder, such as about 200 mg, about 400 mg, about 600 mg, or about 800 mg of lidocaine. For example, a smaller payload may be delivered from a smaller device or from a device loaded with fewer tablets, the remainder of the space in the device being loaded with a spacer or filling material.

In one embodiment, the device has a 50 mg payload of lidocaine hydrochloride monohydrate. The device may provide a release rate up to about 5 mg/day (e.g., at day 3 or 4 after insertion into the bladder) over a treatment period.

In some embodiments, the amount of anesthetic or analgesic agent effective to achieve a desired therapeutic effect is at least 50 mg released continuously over 48 or more hours. In other embodiments, the amount of anesthetic or analgesic agent effective to achieve a desired therapeutic effect is at least 100 mg released continuously over 48 or more hours. In certain embodiments, the amount of anesthetic or analgesic agent effective to achieve a desired therapeutic effect is at least 150 mg released continuously over 48 or more hours. In one embodiment, the amount of anesthetic or analgesic agent effective to achieve a desired therapeutic effect is at least 200 mg released continuously over 48 or more hours. In another embodiment, the amount of anesthetic or analgesic agent effective to achieve a desired therapeutic effect is at least 300 mg released continuously over 48 or more hours. In a further embodiment, the amount of anesthetic or analgesic agent effective to achieve a desired therapeutic effect is at least 400 mg released continuously over 48 or more hours. In yet another embodiment, the amount of anesthetic or analgesic agent effective to achieve a desired therapeutic effect is at least 500 mg released continuously over 48 or more hours. In a still further embodiment, the amount of anesthetic or analgesic agent effective to achieve a desired therapeutic effect is at least 600 mg released continuously over 48 or more hours. In any of these embodiments, the anesthetic or analgesic agent comprises lidocaine.

The foregoing specific configurations are merely possibilities of the type of devices that may be created by a person skilled in the art upon reading the present disclosure. For example, in some embodiments the drug reservoir portion may be omitted completely, and the retention frame portion may be associated with another component for retention in the body, such as the bladder. Examples of other components include diagnostic equipment, test materials, and small electronic devices, such as cameras and sensors, among others.

Method of Making the Device

An embodiment of a method of making an implantable drug delivery device may include forming a drug delivery device, forming a number of drug tablets, and loading the drug tablets into the drug delivery device. In embodiments, forming the drug delivery device may include one or more of the following sub-steps: forming a device body, forming a retention frame, associating the device body with the retention frame, and forming one or more apertures in the device body. Suitable methods are described for example in U.S. Patent Application Publication No. 2010/0330149 to Daniel, et al.; U.S. Patent Application Publication No. 2010/0331770 to Lee et al.; and U.S. Patent Application Publication No. 2011/0060309 to Lee et al., which are incorporated herein by reference.

Use and Applications of the Device

The device may be implanted in a body cavity or lumen, and subsequently may release one or more drugs for the treatment of one or more conditions, locally to one or more tissues at the deployment site and/or regionally to other tissues distal from the deployment site. The release may be controlled over an extended period. Thereafter, the device may be removed, resorbed, excreted, or some combination thereof.

Figure 7:
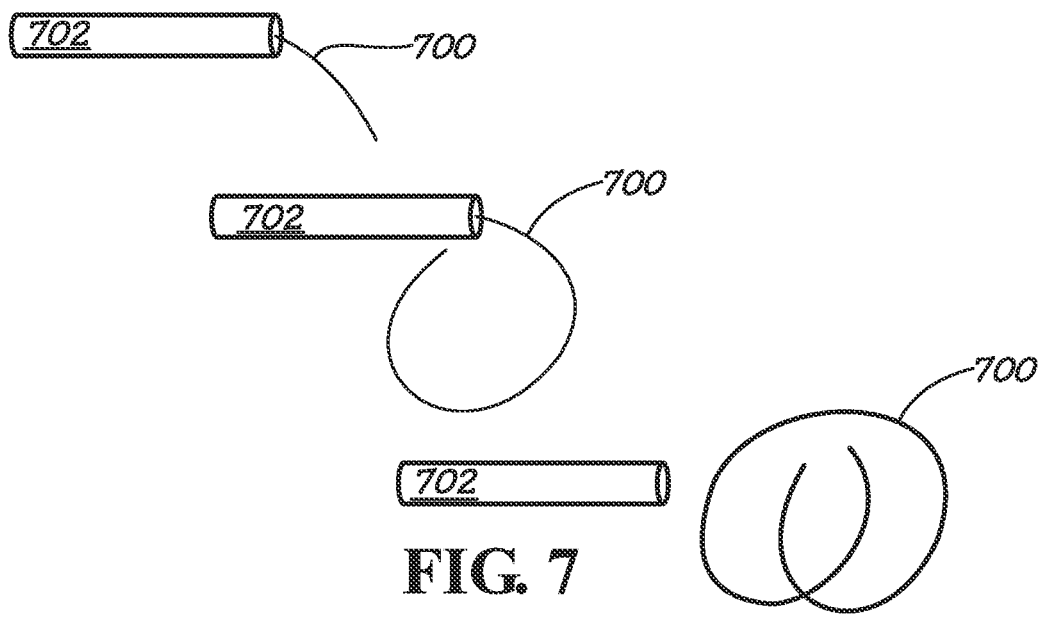
FIG. 7 illustrates a method of implanting a drug delivery device.

In one example, the device is implanted by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. An example is illustrated in FIG. 7, which shows the device 700 assuming a retention shape as the device exits a deployment instrument 702. The deployment instrument 702 may be any suitable lumen device, such as a catheter, urethral catheter, or cystoscope. These terms are used interchangeably herein, unless otherwise expressly indicated. The deployment instrument 1102 may be a commercially available device or a device specially adapted for the present drug delivery devices.

Once implanted, the device may release the drug. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated.

In embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

Subsequently, the device may be retrieved from the body, such as in cases in which the device is non-resorbable or otherwise needs to be removed. Retrieval devices for this purpose are known in the art or can be specially produced. The device also may be completely or partially bioresorbable, such that retrieval is unnecessary, as either the entire device is resorbed or the device sufficiently degrades for expulsion from the bladder during urination. The device may not be retrieved or resorbed until some of the drug, or preferably most or all of the drug, has been released. If needed, a new drug-loaded device may subsequently be implanted, during the same procedure as the retrieval or at a later time.

Figure 8:
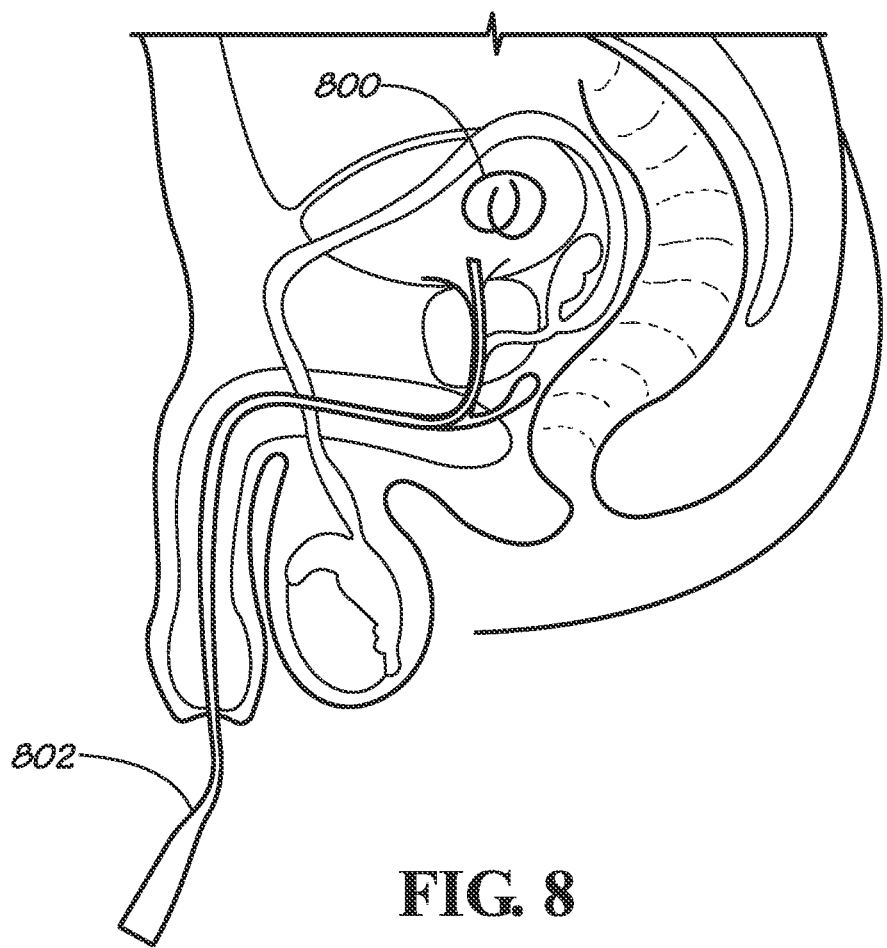
FIG. 8 is a sagittal view of a male patient, illustrating a drug delivery device exiting a deployment instrument into a bladder of the patient.

FIG. 8 illustrates the implantation of a device 800 into the bladder, wherein the adult male anatomy is shown by way of example. A deployment instrument 802 may be inserted through the urethra to the bladder, and the device 800 may be passed through the deployment instrument 802, driven by a stylet or flow of lubricant or other fluid, for example, until the device 800 exits into the bladder. Thus, the device is implanted into the bladder of a male or female human patient in need of treatment, either adult or child.

The device may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one embodiment, the implantable device, with a self-contained drug payload, is deployed wholly within the bladder to provide local, sustained delivery of at least one drug locally to the bladder in an effective amount. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more.

In such cases, the device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain, post-procedural (prostate, urethral, bladder) pain and spasm, irritative voiding symptoms (sense of urgency, urinary frequency, nocturia) or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In some embodiments, the intravesical drug delivery device is deployed into the bladder of a patient for regional drug delivery to one or more nearby genitourinary sites. The device may release drug locally to the bladder and regionally to other sites near the bladder. Such delivery may provide an alternative to systemic administration, which may entail undesirable side effects or result in insufficient bioavailability of the drug.

In one embodiment, the intravesical drug delivery device is implanted into a bladder to locally deliver a local anesthetic agent for management of pain and/or irritative voiding symptoms (urgency, frequency, nocturia) arising from any source, such as a disease or disorder in genitourinary tissues, or pain stemming from any bladder procedure, such as surgery, catheterization, ablation, medical device implantation, or stone or foreign object removal, among others. For example, a local anesthetic agent can be released into the bladder for regional delivery to nearby sites to manage nearby pain arising from any source, such as post-operative pain associated with the passage of a medical device into or through a ureter or other post-operative pain in sites apart from the bladder.

In one particular embodiment, a device having a payload of lidocaine may be delivered to the bladder, and lidocaine may be continuously released from the device over an extended period. In one embodiment, local delivery of lidocaine to the urothelium of the bladder is provided from the presently disclosed devices which have been deployed into the bladder in a manner which achieves a sustained level of lidocaine above the concentration that could be obtained for an extended period via instillation, yet without the high initial peak observed with instillation and without significant systemic concentrations. Thereby, a small payload may be implanted, reducing the risk of systemic effects in the event of device failure. Implanting lidocaine in solid form permits further reducing the size of the device to reduce bladder irritation and patient discomfort. The lidocaine may be delivered without regard to the pH of the urine. In one embodiment, the device may have two payloads of lidocaine that are released at different times. The first payload may be adapted for relatively quick release, while the second payload may be adapted for more continuous release. For example, the first payload may be in liquid form or may be housed in a relatively fast-acting osmotic pump, such as a silicone tube having a relatively thinner wall, while the second payload may be solid form or may be housed in an osmotic pump that experiences an initial delay or induction time before releasing, such as a silicone tube having a relatively thicker wall. Thus, the method may continuously release lidocaine into the bladder during an initial, acute phase and during a maintenance phase. Such a method may compensate for an initial induction time of the device.

The present invention may be further understood with reference to the following non-limiting examples.

Example 1: Diffusion of Drug Through the Wall of a Drug Reservoir

A study was performed to determine the feasibility of delivering drug through the wall of a drug reservoir via diffusion. Devices were formed form silicone tubes having an inner diameter of about 0.060 inches, an outer diameter of 0.076 inches, and a length of about 3 cm. The devices were loaded with solid drug tablets of lidocaine, for a total payload of about 60 mg. Some of the devices included an aperture formed through the tube wall, the aperture having a diameter of 150 µm. These devices were loaded with solid tablets of either lidocaine hydrochloride monohydrate or a combination of lidocaine hydrochloride monohydrate and lidocaine base. Other devices did not include an aperture and were loaded with solid drug tablets of lidocaine base. The devices were tested in vitro in water at about 37° C. Release profile data demonstrated that it is feasible to deliver drug via diffusion through a silicone wall without an aperture. The release rate was relatively zero-order over a period of about four days, tapering off thereafter, with the release rate varying based on the device.

Another study was performed to investigate the feasibility of delivering drug from a device through both a wall of a drug reservoir and from an aperture in the wall of the drug reservoir. Devices were formed form silicone tubes having a length of about 3 cm. The devices were loaded with solid drug tablets of lidocaine base, for a total payload of about 60 mg. Five devices had an inner diameter of about 0.060 inches and an outer diameter of 0.076 inches. The first device had one aperture with a diameter of about 150 µm, the second device had two apertures that each had a diameter of about 360 µm, the third device had thirty apertures that each had a diameter of about 360 µm, the fourth device had sixty apertures that each had a diameter of about 360 µm, and the fifth device had no apertures. A sixth device had an inner diameter of about 0.062 inches, an outer diameter of about 0.095 inches, and no apertures. The devices were tested in vitro in water at about 37° C. Release profile data showed that lidocaine base can be released from a silicone tube without any apertures and that the release rate can be increased by adding apertures to the device.

Example 2: Effectiveness of Device Versus Daily Instillations of Lidocaine

An open-label, ascending dose, active-treatment cohort study was conducted to investigate safety, tolerability, and limited pharmacokinetic characterization of the device. The device was cytoscopically inserted into the bladders of 16 white, non-Hispanic female patients suffering from interstitial cystitis (IC) (2 patients were treated in both cohorts). Nine patients in each cohort received devices containing 200 mg and 650 mg of lidocaine, respectively. The 200 mg and 650 mg devices contained 246 mg and 801 mg of lidocaine hydrochloride monohydrate, respectively. The 200 mg device included silicone elastomer tubing, nitinol wire, and sapphire (aluminum oxide) balls. The 650 mg device included the same components, except the sapphire balls were replaced by silicone spacers and silicone adhesive.

On Day 1 of the test, a 200 mg or 650 mg device was inserted into the bladder of each patient. On Day 14±1, the devices were removed by cystoscopy. Each patient received a follow-up examination on Day 21±2 and Day 28±2.

Before insertion of the device, the participants scored their bladder pain and urinary urgency on a scale of "0 to 10" on a 10 cm line with 0 and 10 representing "no pain or urgency" and "pain or urgency the worst you can imagine," respectively. The baseline results are shown in Table 1, along with the baseline voiding frequency per 24 hours, baseline nocturia, interstitial cystitis symptom index (ICSI), and interstitial cystitis problem index (ICPI).

TABLE 1

Disease Criteria Scores Before Testing

| Criteria | Baseline Score (±Stand. Dev.) |
| --- | --- |
| Pain (0-10) | 7.3 ± 1.4 |
| Urgency (0-10) | 7.7 ± 1.0 |
| Voiding Frequency (Per 24 Hours) | 19 ± 5.5 |
| Nocturia | 5.0 ± 2.5 |
| ICSI | 14 ± 3.24 |
| ICPI | 12.3 ± 3.04 |

The patients were asked to reassess the scores in Table 1 on Days 1, 2, 3, 7, 10, 14±1, 21±2, and 28±2 of the study. On those same days, blood and urine samples were collected and analyzed for lidocaine and its metabolite—2,6-xylidene—using separate validated LC-MS/MS assays. The assays' results are shown in Tables 2, 3, and 4. Two patients in the 200 mg device cohort did not meet the definition of PK evaluable and were excluded (hence, n=9-2=7), however, the full 650 mg device cohort was evaluated (hence, n=9).

TABLE 2

Urinary Recovery Of Lidocaine (µg) and 2,6-Xylidene After Insertion

| | 200 mg device (n = 7) | | | | 650 mg (n = 9) | | | |
| --- | --- | --- | --- | --- | --- | --- | --- | --- |
| | Lidocaine (µg) | | 2,6-Xylidene (µg) | | Lidocaine (µg) | | 2,6-Xylidene (µg) | |
| Day | Mean | SD | Mean | SD | Mean | SD | Mean | SD |
| 1 | 0.00 | 0.00 | 0.00 | 0.00 | 0.00 | 0.00 | 0.00 | 0.00 |
| 2 | 13455.55 | 1173.29 | 5.24 | 3.95 | 11194.72 | 9888.95 | 8.59 | 10.60 |
| 3 | 21371.86 | 1269.00 | 4.41 | 2.28 | 42840.75 | 19949.81 | 17.74 | 25.53 |
| 7 | 5740.11 | 4538.56 | 1.45 | 0.95 | 18447.90 | 9407.19 | 13.58 | 13.44 |
| 10 | 3656.14 | 2440.04 | 0.25 | 0.44 | 15453.06 | 12889.94 | 6.34 | 7.70 |
| 14 | 2592.89 | 1553.65 | 0.00 | 0.00 | 4538.72 | 4601.83 | 3.66 | 7.34 |
| 21 | 5.08 | 13.43 | 0.00 | 0.00 | 0.00 | 0.00 | 0.00 | 0.00 |
| 28 | 0.00 | 0.00 | 0.00 | 0.00 | 0.00 | 0.00 | 0.00 | 0.00 |

TABLE 3

Urinary Recovery of Lidocaine (% dose) and 2,6-Xylidene After Insertion

| | 200 mg device (n = 7) | | | | 650 mg (n = 9) | | | |
| --- | --- | --- | --- | --- | --- | --- | --- | --- |
| | Lidocaine (% dose) | | 2,6-Xylidene (% dose) | | Lidocaine (% dose) | | 2,6-Xylidene (% dose) | |
| Day | Mean | SD | Mean | SD | Mean | SD | Mean | SD |
| 1 | 0.00 | 0.00 | 0.00 | 0.00 | 0.00 | 0.00 | 0.00 | 0.00 |
| 2 | 6.73 | 0.59 | 0.01 | 0.00 | 1.72 | 1.52 | 0.00 | 0.00 |
| 3 | 10.69 | 0.63 | 0.00 | 0.00 | 6.59 | 3.07 | 0.01 | 0.01 |
| 7 | 2.87 | 2.27 | 0.00 | 0.00 | 2.84 | 1.45 | 0.00 | 0.00 |
| 10 | 1.83 | 1.22 | 0.00 | 0.00 | 2.38 | 1.98 | 0.00 | 0.00 |
| 14 | 1.30 | 0.78 | 0.00 | 0.00 | 0.70 | 0.71 | 0.00 | 0.00 |
| 21 | 0.00 | 0.01 | 0.00 | 0.00 | 0.00 | 0.00 | 0.00 | 0.00 |
| 28 | 0.00 | 0.00 | 0.00 | 0.00 | 0.00 | 0.00 | 0.00 | 0.00 |

TABLE 4

Plasma Concentrations of Lidocaine and 2,6-Xylidene

| | 200 mg device (n = 7) | | | | 650 mg (n = 9) | | | |
|---|---|---|---|---|---|---|---|---|
| | Lidocaine (ng/mL) | | 2,6-Xylidene (ng/mL) | | Lidocaine (ng/mL) | | 2,6-Xylidene (ng/mL) | |
| Day | Mean | SD | Mean | SD | Mean | SD | Mean | SD |
| 1 | 0.10[+] | 0.26 | 0.00 | 0.00 | 0.00 | 0.00 | 0.00 | 0.00 |
| 2 | 6.40 | 5.35 | 0.47 | 0.46 | 3.66 | 2.82 | 0.29 | 0.29 |
| 3 | 4.97 | 2.89 | 0.37 | 0.26 | 12.09 | 19.33 | 0.93 | 1.27 |
| 7 | 1.15 | 1.37 | 0.11 | 0.10 | 9.40 | 10.77 | 0.82 | 0.57 |
| 10 | 0.58 | 0.64 | 0.04 | 0.07 | 4.30 | 7.18 | 0.29 | 0.28 |
| 14 | 1.01 | 2.40 | 0.00 | 0.00 | 1.26 | 1.75 | 0.10 | 0.15 |
| 21 | 0.36[++] | 0.88 | 0.03[++] | 0.06 | 0.00 | 0.00 | 0.00 | 0.00 |
| 28 | 0.00 | 0.00 | 0.00 | 0.00 | 0.00 | 0.00 | 0.00 | 0.00 |

[+]One patient had a lidocaine plasma concentration of 0.68 ng/mL.
[++]One patient had a lidocaine and 2,6-xylidene plasma concentration of 2.15 and 0.15 ng/mL, respectively.

Based on urinary recovery and observed plasma concentrations in Tables 2, 3, and 4 lidocaine was recovered in each test during the first 14 days after insertion, suggesting that the drug was continuously released during the entire period.

After the devices were removed on Day 14, the amount of lidocaine in the blood and urine samples quickly diminished. Tables 2 and 3 indicate that an average of 5.08 µg and 0.00 µg of lidocaine were recovered on Days 21 and 28, respectively, of the study. Both of these values represented 0.00% of the original lidocaine dose. Table 4 indicates that the plasma concentrations of lidocaine diminished to zero by Days 21 and 28 after removal of the device on Day 14.

Despite the removal of the device on Day 14 and the subsequent diminishment of lidocaine from the blood and urine samples, the patients enjoyed sustained therapeutic benefits, including less pain and urgency, beyond Day 14 of the study.

Figure 11:
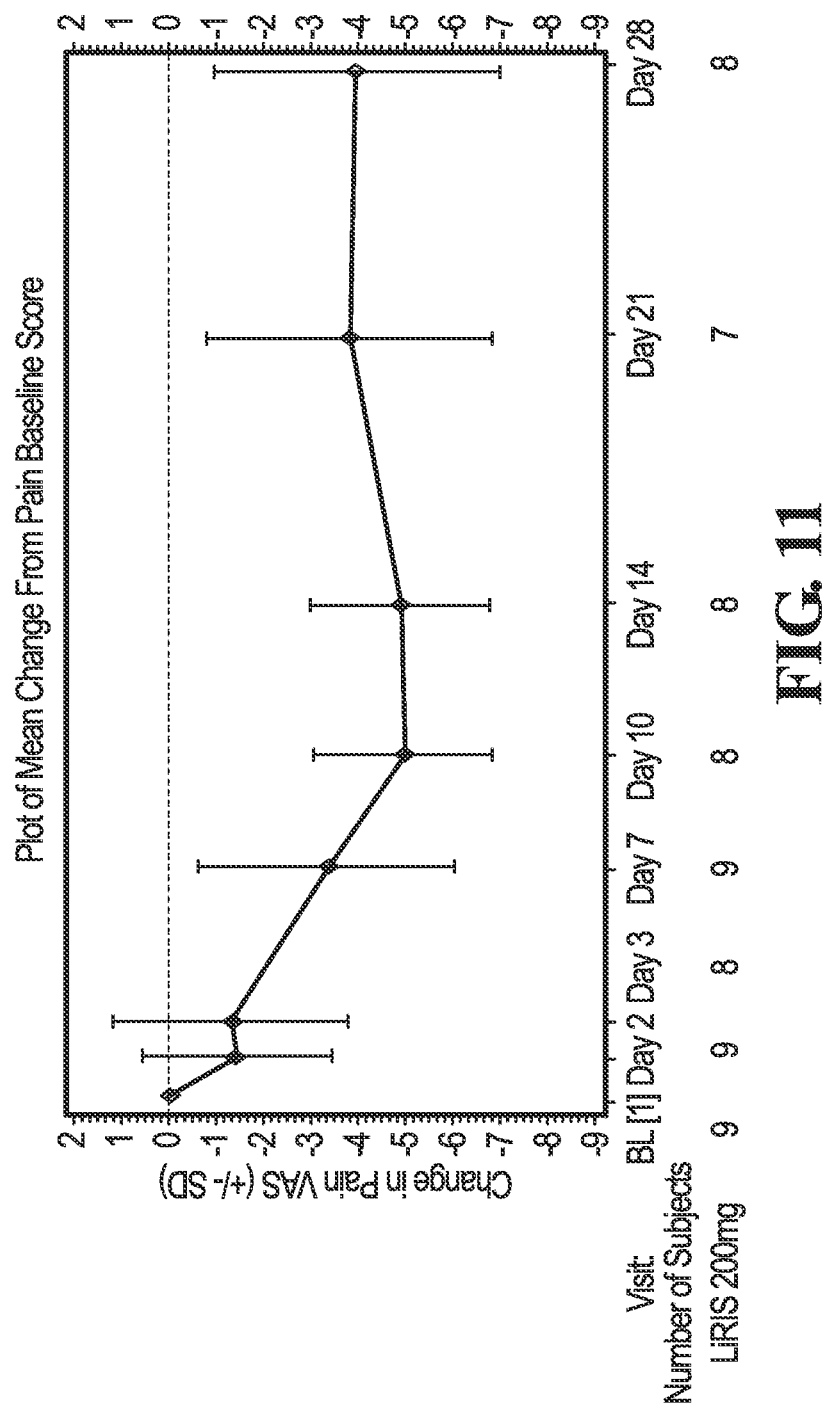
FIGS. 11-14 are graphs showing various baseline improvement scores achieved with an embodiment of a drug delivery device.

FIG. 11 shows the sustained reduction in bladder pain that occurred throughout the study for patients receiving the 200 mg device. The "0" line represents the baseline pain score of 7.3±1.4. Although the maximum change from the baseline of −4.9±1.89 occurred on Day 10, reductions of about −3.6±3 and about −3.8±3 occurred on Days 21 and 28, respectively. The sustained reduction of the baseline pain score after Day 14 suggested that the lidocaine's therapeutic effect extended beyond the treatment period. The data in FIG. 11 contrasted with a trial that tested the effects of lidocaine bladder instillations given daily (1 hour) for five days. The daily instillation trial showed a maximum baseline reduction in bladder pain of only −2.38±2.67 (Nickel, J. Curtis et al. "*Intravesical alkalinized lidocaine (PSD597) offers sustained relief from symptoms of interstitial cystitis and painful bladder symdrome*," Journal Compilation, BJU International 103, 2008, 910-918) (hereinafter "Plethora").

Figure 12:
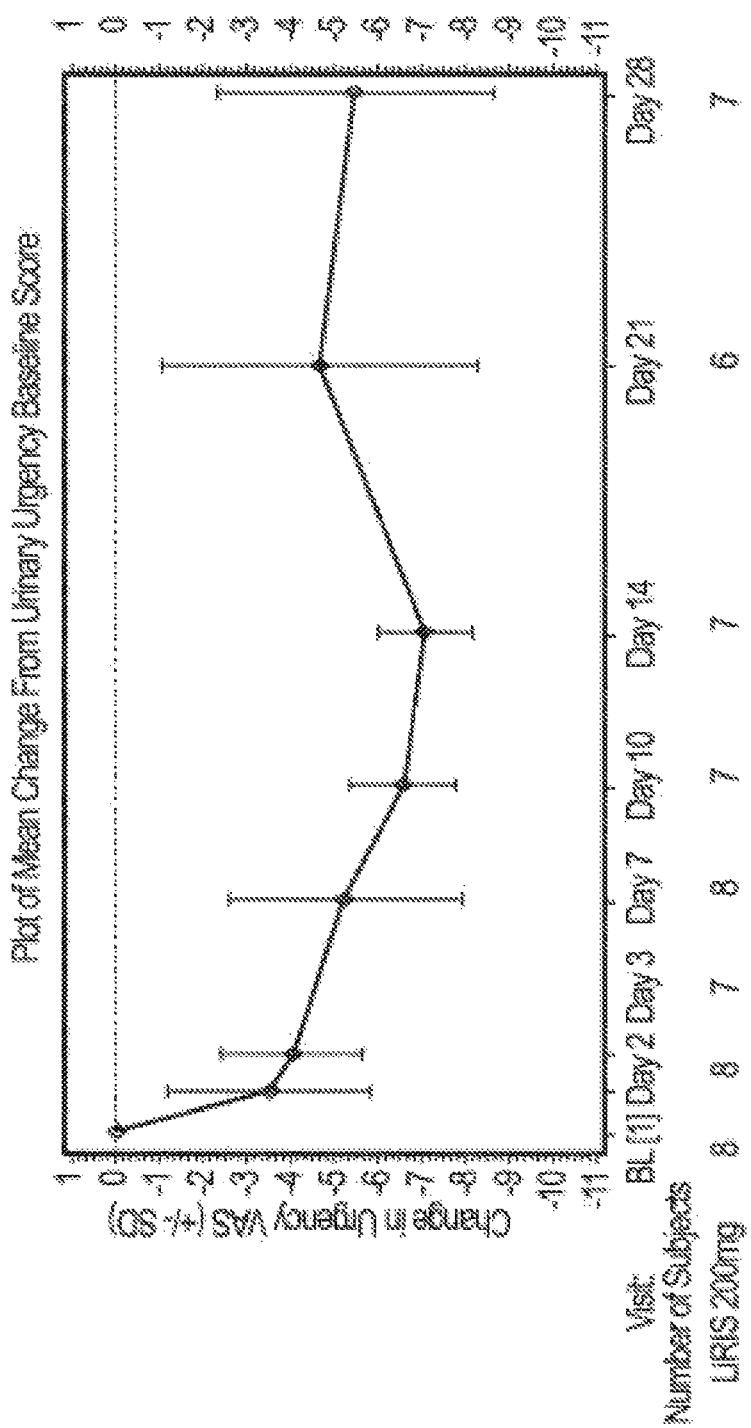

A sustained reduction of baseline urgency scores also was observed. FIG. 12 shows the sustained reduction in urinary urgency that occurred throughout the study for the patients receiving the 200 mg device. The "0" line represents the baseline urgency score of 7.7±1.0. Although the maximum change from baseline of −7.0±1.08 occurred on Day 14, reductions of about −4.4±3.6 and about −5.2±3 occurred on Days 21 and 28, respectively. Once again, the data in FIG. 12 represented a significant improvement over Plethora's daily instillation test, which showed a maximum reduction in urinary urgency of only −2.09±2.14.

Figure 13:
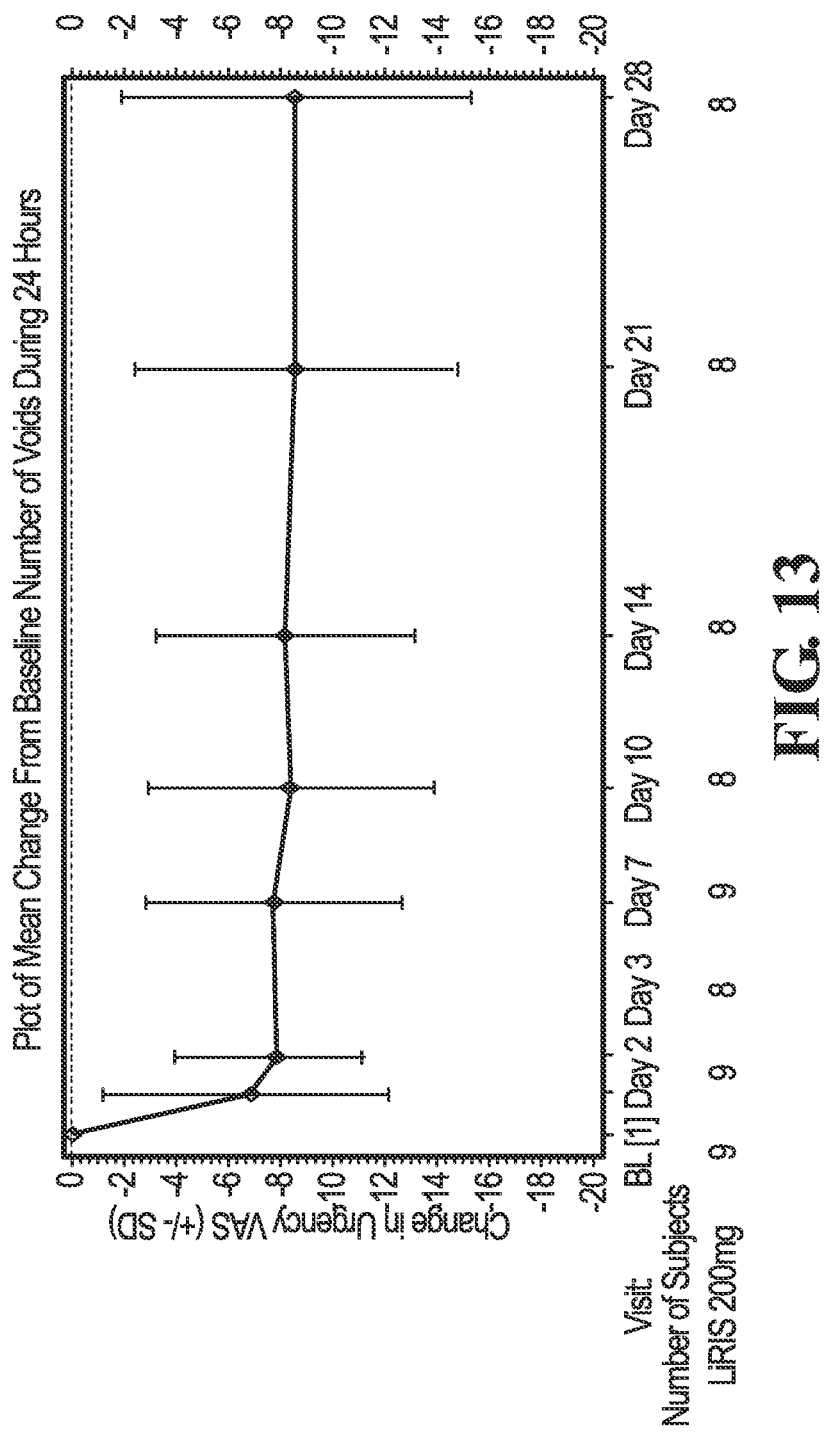

The frequency of voiding also was reduced almost immediately after device deployment and was sustained after the device removal on Day 14, as shown in FIG. 13. The "0" line represents the baseline voiding frequency of 19±5.5. From Day 3 to Day 28, the device reduced the average voiding frequency by about −8.0±3.9 despite the removal of the device on Day 14. In contrast, Plethora's daily instillation test reduced voiding frequency by −1.69±7.62 only.

Figure 14:
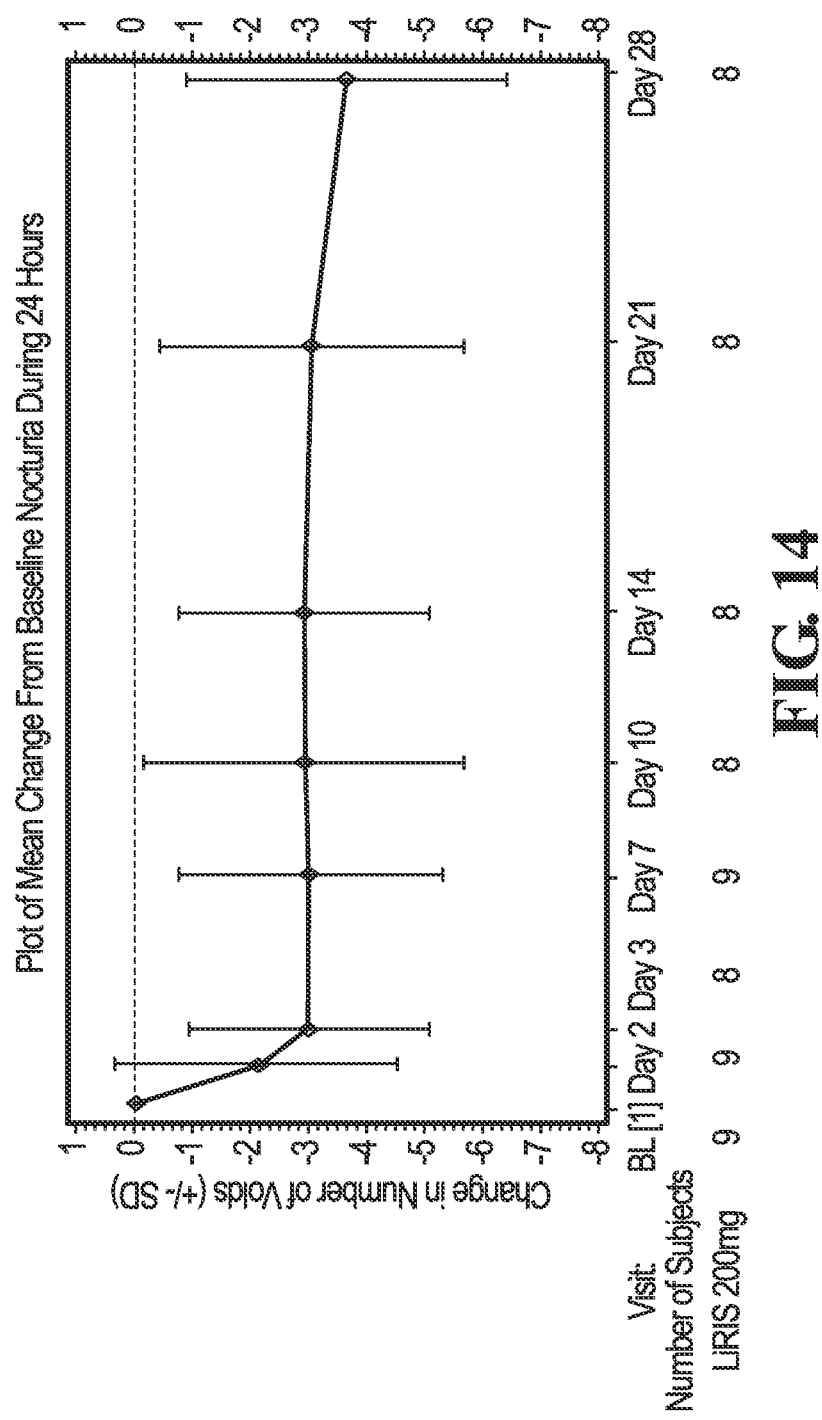

The device also reduced baseline nocturia by an average of about 3±2.2 by Day 14. As shown in FIG. 14, the device reduced nocturia soon after deployment and maintained a sustained effect after its removal on Day 14. Nocturia data were not collected in the Plethora trial.

Figure 15:
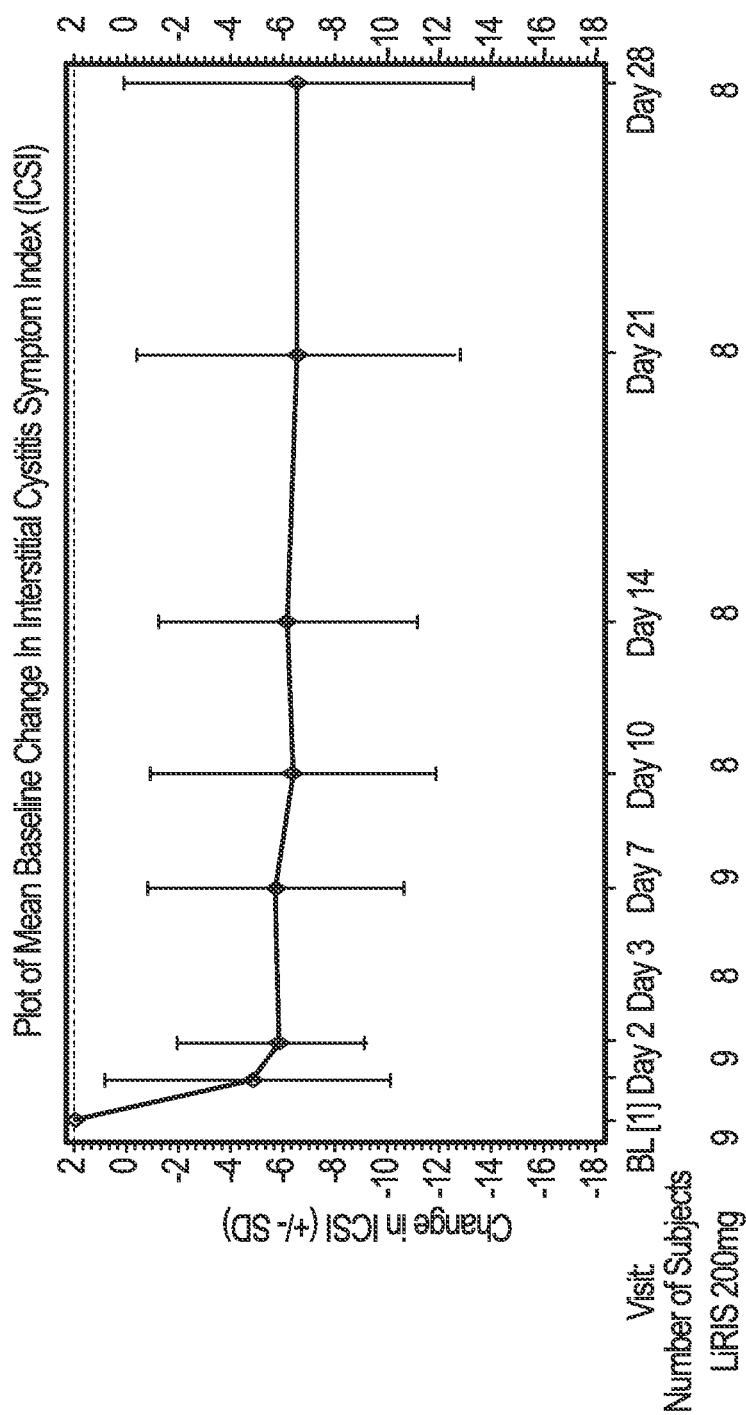
FIGS. 15-19 are graphs showing various index scores achieved with an embodiment of a drug delivery device.
Figure 16:
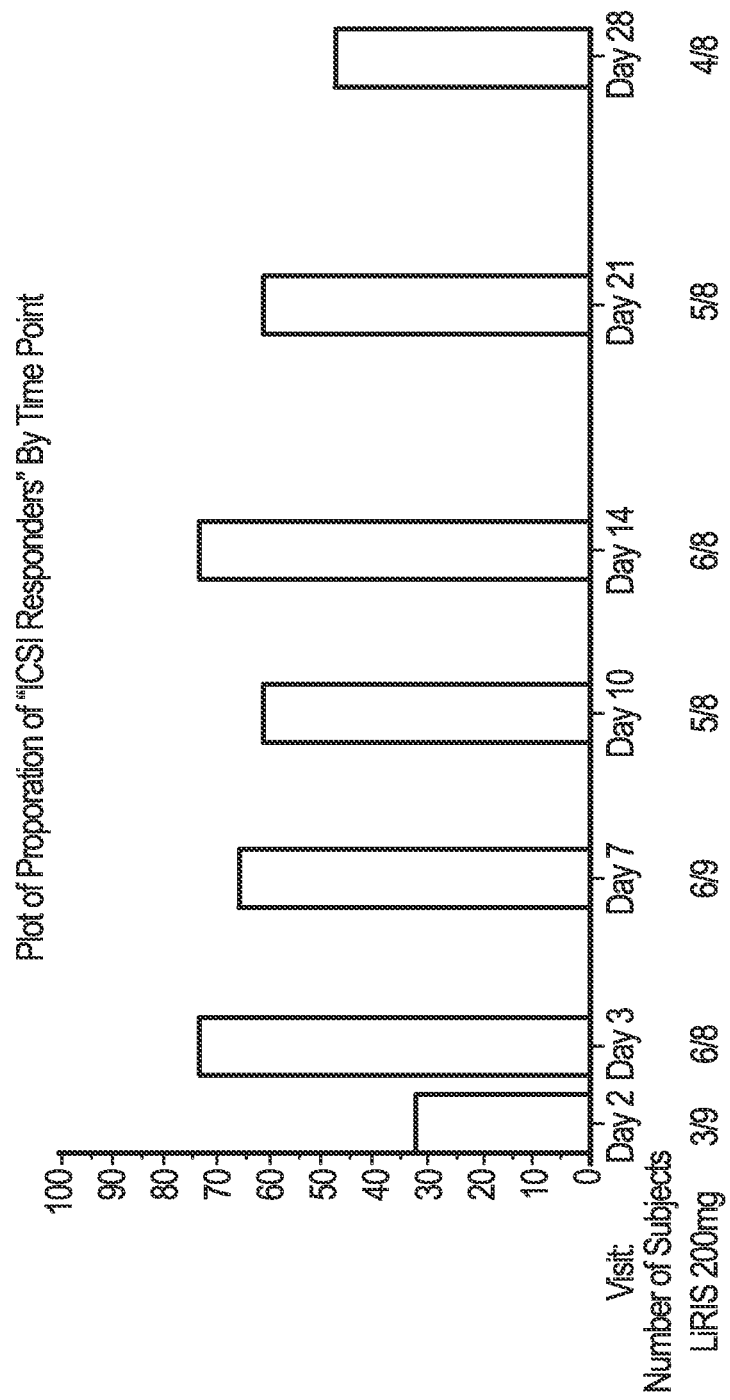

The Plethora trial did show that baseline reduction in ICSI with lidocaine instillations was not sustained following completion of treatment. The baseline ICSI in the Plethora trial was 13.67±2.99 and 13.60±3.09. The baseline ("0" line) ICSI in the current trial was 14±3.24, which was consistent with severe disease and similar to the baseline in the Plethora trial. Unlike the Plethora trial's daily instillations, however, the 200 mg device caused a sustained reduction in baseline ICSI after the device was removed from the bladder. The baseline reduction of ICSI throughout the study is shown in FIG. 15. FIG. 16 shows the proportion of "ICSI Responders" in the cohort at each time point. An "ICSI Responder" was defined as a patient with a 30% or greater improvement from the baseline score.

Figure 17:
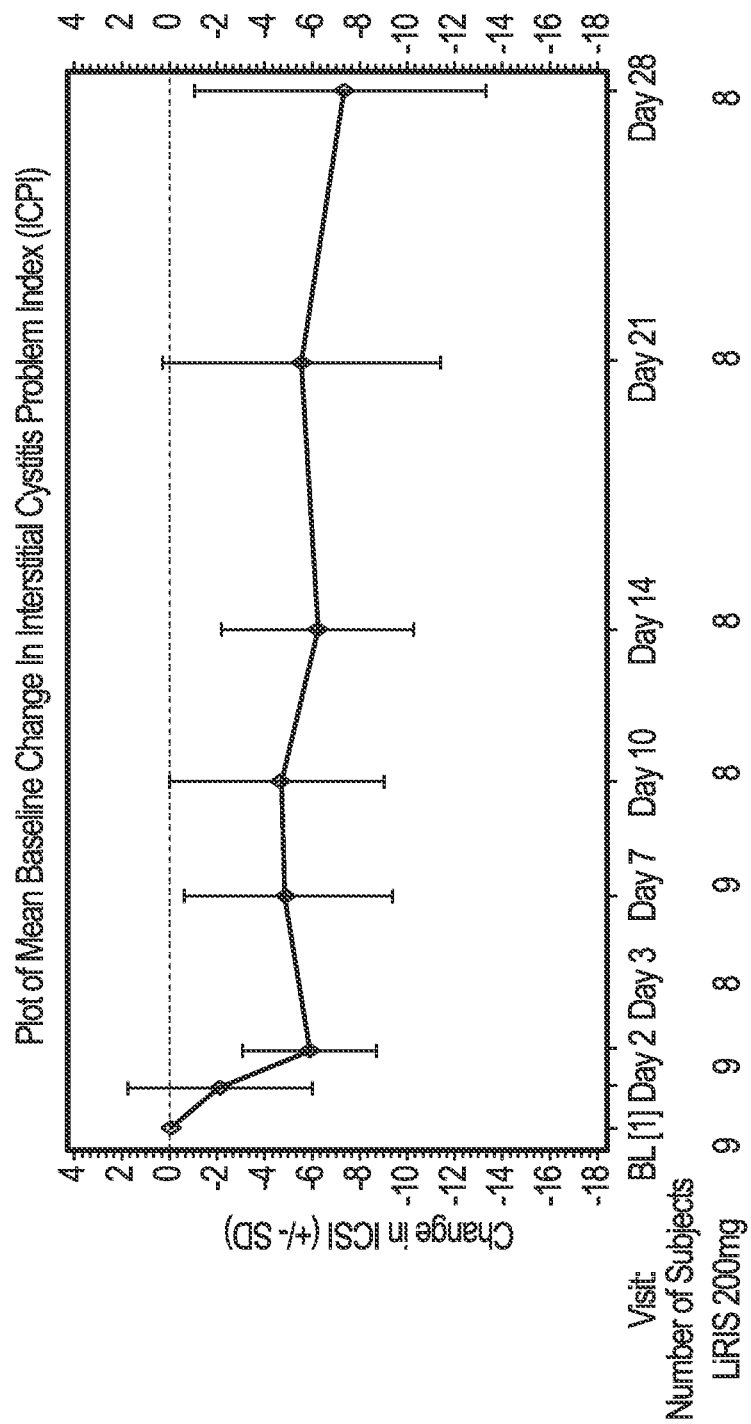
Figure 18:
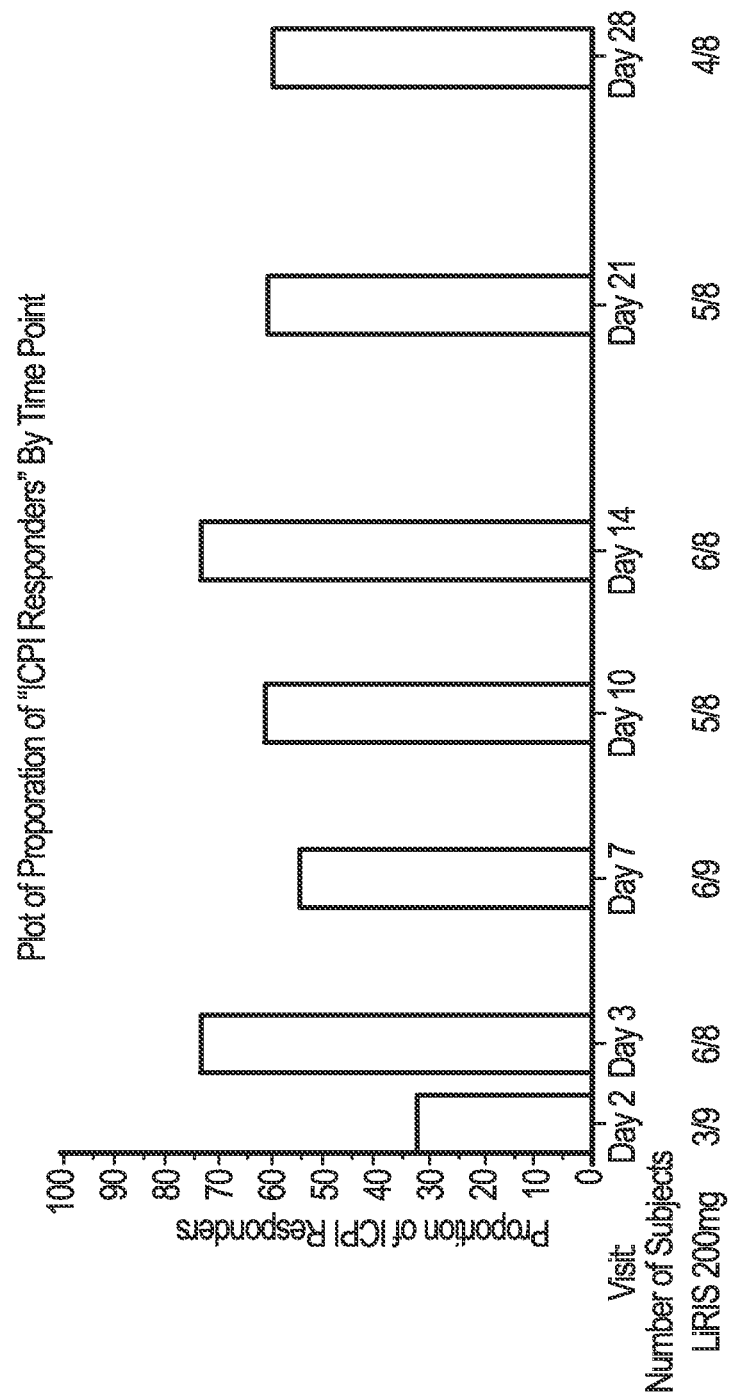

Similarly, the 200 mg device caused a sustained reduction in the ICPI throughout the study, including after the removal of the device on Day 14. The baseline ("0" line) ICPI was 12.3±3.04, which is shown as the "0" line in FIG. 17. As shown in FIG. 17, the average baseline reduction of ICPI caused by the 200 mg device averaged more than about −4 from Day 3 to Day 28. The proportion of "ICPI Responders" in the cohort at each time point is shown in FIG. 18. An "ICPI Responder" is defined as one with a 30% or greater improvement from baseline score. In contrast, the Plethora trial had a baseline ICPI of 12.09±2.50 and 12.22±2.28, but the mean baseline reductions on Days 8 and 15 were only −3.82±3.61 and −3.36±3.90, respectively.

Figure 19:
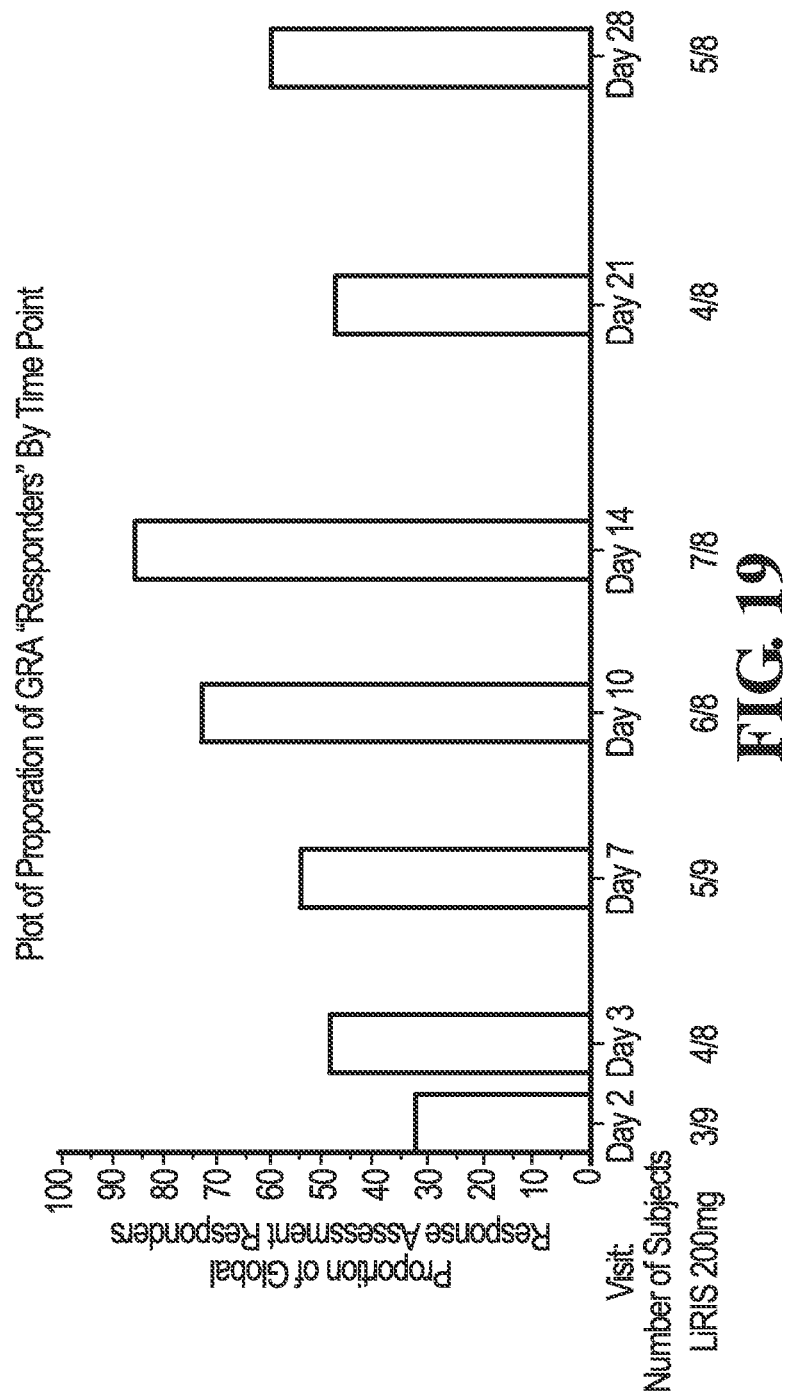
Figure 20:
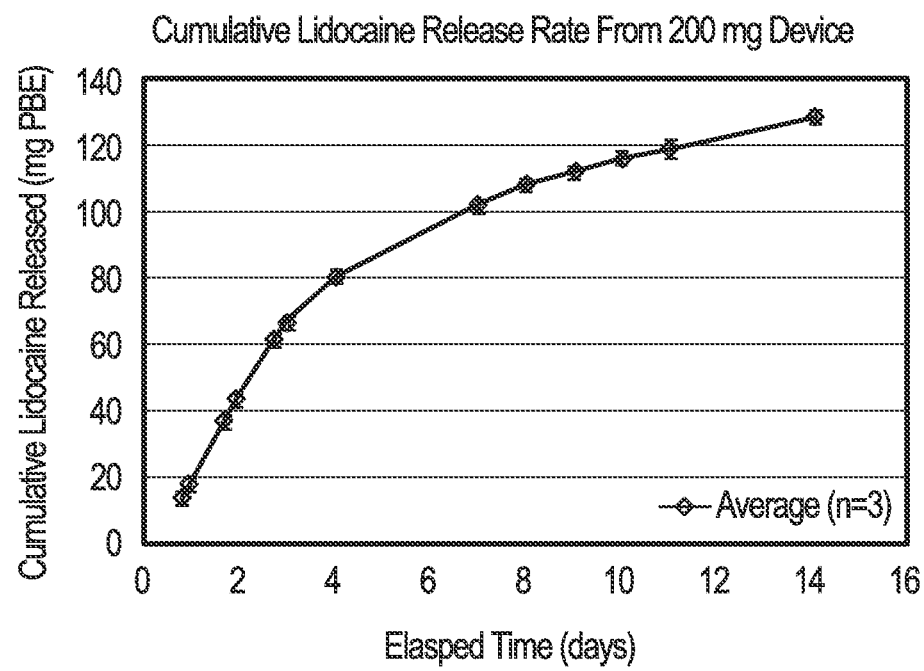
FIG. 20 is a graph showing cumulative release of lidocaine over a treatment period, according to one embodiment.
Figure 21:
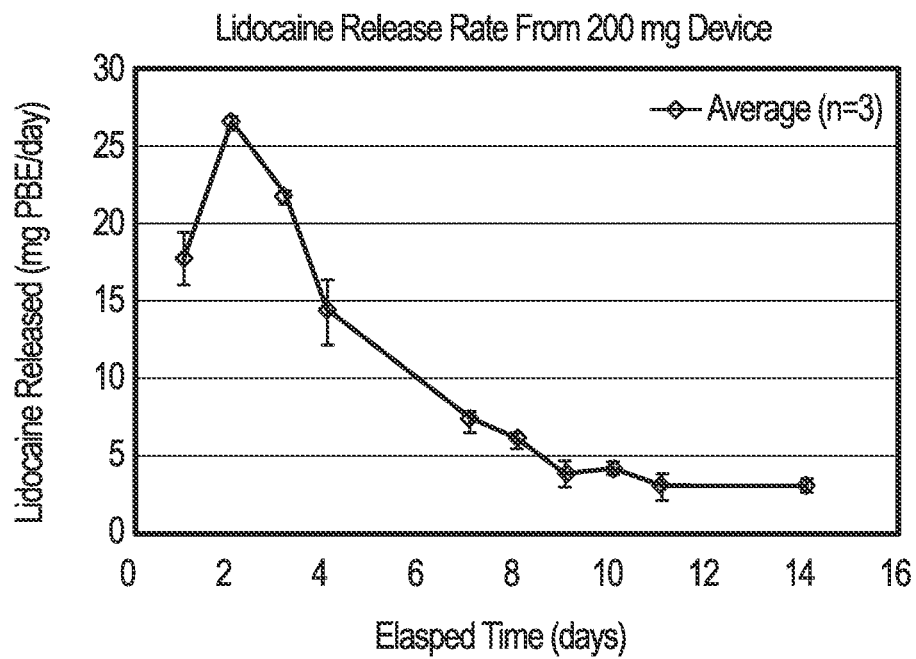
FIG. 21 is a graph showing lidocaine release rate according to one embodiment.
Figure 22:
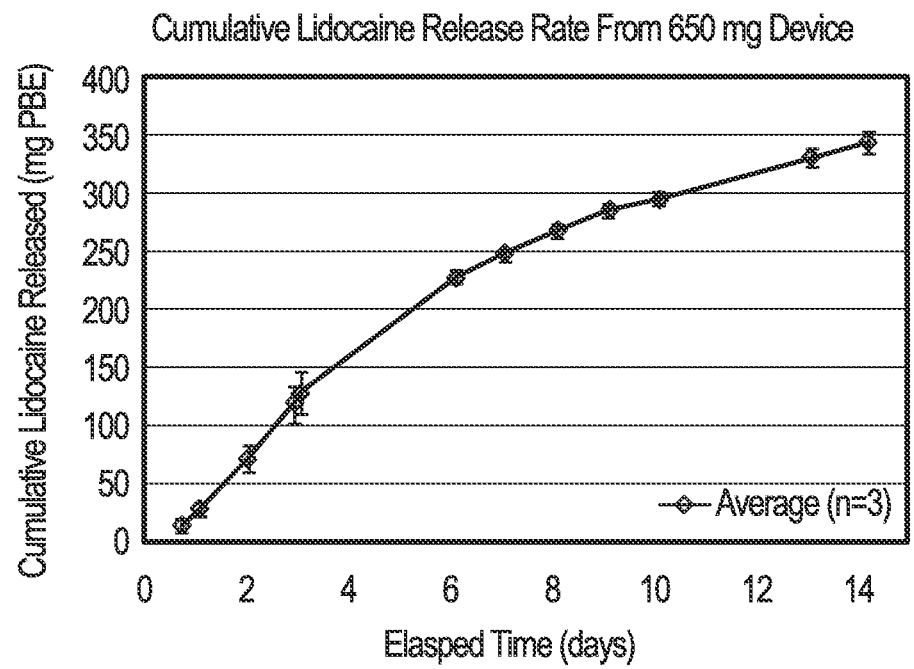
FIG. 22 is a graph showing cumulative release of lidocaine over a treatment period, according to one embodiment.
Figure 23:
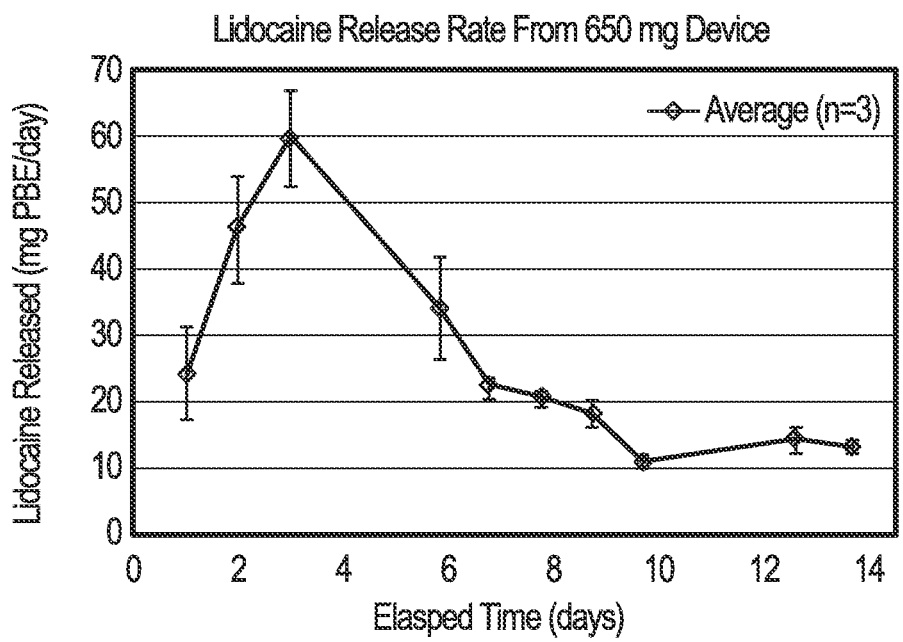
FIG. 23 is a graph showing lidocaine release according to one embodiment.

A Global Response Assessment (GRA) test also was administered to the patients at Days 2, 3, 7, 10, 14, 21, and 28. A GRA is a seven item Likert scale where patients report their overall response as (1) markedly worse, (2) moderately worse, (3) mildly worse, (4) no change, (5) mildly improved, (6) moderately improved, or (7) markedly improved. A "Responder" is a patient whose response is either "moderately" or "markedly improved." The percentage of "Responders" at each time point is shown in FIG. 19, and averaged about 50% or more on Days 3 through 28. In the Plethora trial, instillations of lidocaine—even when administered daily for five days—induced responses of "moderately" or "markedly" global improvement in 44-63% of IC patients when tested in a similar open-label design.

Example 3: Release Rate of Lidocaine From Device

The release rate of lidocaine from the 200 mg and 650 mg devices of Example 2 was measured in vitro by simulating bladder conditions. Tables 5 and 6 depict the average lidocaine release rate (mg free base equivalent (FBE)/day) over 14 days.

TABLE 5

Release Rate of Lidocaine From 200 mg Device

| Elapsed Time (days) | Average Lidocaine Release Rate (mg FBE/day) | Standard Deviation (mg FBE/day) |
|---|---|---|
| 1 | 17.9 | 1.7 |
| 2 | 26.9 | 0.2 |
| 3 | 22.1 | 0.3 |
| 4 | 14.6 | 2.2 |
| 7 | 7.3 | 0.7 |
| 8 | 6.3 | 0.6 |
| 9 | 4.0 | 0.9 |
| 10 | 4.4 | 0.4 |
| 11 | 3.2 | 0.9 |
| 14 | 3.3 | 0.4 |
| Average | 11 mg/day | |

TABLE 6

Release Rate of Lidocaine From 650 mg Device

| Elapsed Time (days) | Average Lidocaine Release Rate (mg FBE/day) | Standard Deviation (mg FBE/day) |
|---|---|---|
| 1 | 24.9 | 6.8 |
| 2 | 46.4 | 7.9 |
| 3 | 59.7 | 7.0 |
| 6 | 33.8 | 7.9 |
| 7 | 21.9 | 0.8 |
| 8 | 19.8 | 1.4 |
| 9 | 17.6 | 1.9 |
| 10 | 10.2 | 0.8 |
| 13 | 13.1 | 0.2 |
| 14 | 12.2 | 1.1 |
| Average | 26 mg/day | |

The cumulative lidocaine release rates and lidocaine release rates for the 200 mg and 650 mg devices are plotted in FIGS. 20 and 21, and FIGS. 22 and 23, respectively.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A device for administering lidocaine continuously to a patient's bladder, the device comprising:
   an elastic device body which comprises a tube which comprises a water-permeable material and defines a reservoir, the tube having a single aperture having a diameter between 100 μm and 200 μm;
   a plurality of solid tablets disposed in the reservoir, wherein the plurality of solid tablets comprises from 150 mg to 1000 mg lidocaine, in a water-soluble salt form,
   wherein the device body is configured to permit water to enter the reservoir through the water permeable material and solubilize the lidocaine and to provide continuous controlled release of the lidocaine from the device body, driven by osmotic pressure, over a treatment period of 48 hours or more in an amount effective to achieve a therapeutic effect which is sustained beyond the end of the treatment period, and
   wherein the device body is configured to release over the treatment period a mean average amount of from about 5 mg to about 30 mg lidocaine Free Base Equivalent (FBE) per day through the single aperture.

2. The device of claim 1, which is configured to release the lidocaine at a rate in a range from 15 mg to 30 mg lidocaine (FBE) per day over a first 1 to 4 days of the treatment period and at a rate in a range from 15 mg to 3 mg lidocaine (FBE) per day over a remainder of the treatment period.

3. The device of claim 1, which is configured to release the lidocaine at a rate in a range from 25 mg to 60 mg lidocaine (FBE) per day over a first 1 to 6 days of the treatment period and at a rate in a range from 25 mg to 10 mg lidocaine (FBE) per day over a remainder of the treatment period.

4. The device of claim 1, which is configured to release a cumulative amount of from 200 mg to about 400 mg lidocaine (FBE).

5. The device of claim 1, which is configured to release the lidocaine continuously from 2 to 28 days.

6. The device of claim 5, which is configured to release a mean average amount of from about 10 mg to about 30 mg lidocaine (FBE) per day over the treatment period.

7. The device of claim 1, which is configured to release the lidocaine continuously from 3 to 21 days.

8. The device of claim 1, which is configured to release the lidocaine continuously from 10 to 14 days.

9. The device of claim 1, which is configured to release the lidocaine at a rate in a range from 20 mg to 70 mg lidocaine (FBE) per day over a first 1 to 6 days of the treatment period and at a rate in a range from 25 mg to 10 mg lidocaine (FBE) per day over a remainder of the treatment period.

10. The device of claim 1, wherein the plurality of solid tablets comprises lidocaine hydrochloride monohydrate.

11. The device of claim 10, wherein the tube is a silicone elastomer tube and the plurality of tablets are disposed in a lumen in the silicone elastomer tube.

12. The device of claim 11, which comprises from 246 mg to 801 mg of lidocaine hydrochloride monohydrate.

13. The device of claim 12, which is configured to release the lidocaine hydrochloride monohydrate continuously from 2 to 28 days, at a mean average amount of from about 5 mg to about 30 mg lidocaine (FBE) per day over the treatment period.

14. The device of claim 1, wherein:
   the plurality of tablets comprises at least 80 wt % lidocaine hydrochloride;
   the device body is configured to permit the tablets to contact urine in the bladder of a human patient, solubilizing the lidocaine hydrochloride within the device body;
   the device body is configured to permit the solubilized lidocaine hydrochloride to be released, through an aperture in the tube, from the device body continuously over a treatment period that is from 7 days to 21 days; and
   a cumulative amount of the lidocaine released over the treatment period is from about 200 mg to about 600 mg.

15. The device of claim 14, which is configured to release about 400 mg lidocaine over a treatment period of 14 days.

16. A device for administering lidocaine continuously to a patient's bladder, the device comprising:
   a silicone elastomer tube which comprises an annulus defining a reservoir;
   a plurality of solid tablets disposed in the reservoir, the tablets comprising at least 80 wt % lidocaine hydrochloride,
   wherein the tube is configured to permit water to enter the reservoir through a water permeable wall and solubilize the tablets and to release of the solubilized lidocaine from a single aperture in the wall, driven by osmotic pressure, and wherein the device is configured to release a cumulative amount of the lidocaine from about 200 mg to about 600 mg and to release the lidocaine at an average amount from 5 mg to about 30 mg lidocaine (FBE) per day over a period in which the device is deployed in the patient's bladder, wherein the single aperture has a diameter between 100 μm and 200 μm.

* * * * *